United States Patent
Burnett

[19]

[11] Patent Number: 6,065,348
[45] Date of Patent: May 23, 2000

[54] METHOD OF DETECTING CORROSION IN PIPELINES AND THE LIKE BY COMPARATIVE PULSE PROPAGATION ANALYSIS

[75] Inventor: Gale D. Burnett, Lynden, Wash.

[73] Assignee: Profile Technologies, Inc., Pearl River, N.Y.

[21] Appl. No.: 09/090,800

[22] Filed: Jun. 4, 1998

[51] Int. Cl.[7] .................................................. G01N 29/04
[52] U.S. Cl. ................................ 73/801; 73/579; 73/600
[58] Field of Search ............................ 73/577, 579, 588, 73/598, 600, 621, 625, 638, 801; 324/637

[56] References Cited

U.S. PATENT DOCUMENTS

| | | | |
|---|---|---|---|
| 4,130,646 | 12/1978 | Vogt et al. ................................ | 514/255 |
| 4,181,882 | 1/1980 | Isaacs et al. .......................... | 205/775.5 |
| 4,970,467 | 11/1990 | Burnett .................................... | 324/637 |
| 5,456,113 | 10/1995 | Kwun et al. .............................. | 73/587 |
| 5,457,994 | 10/1995 | Kwun et al. .............................. | 73/587 |
| 5,497,661 | 3/1996 | Stripf et al. ............................... | 73/611 |

*Primary Examiner*—Max Noori
*Attorney, Agent, or Firm*—Robert B. Hughes; Hughes & Schacht, P.S.

[57] ABSTRACT

A method of detecting corrosion on an elongate member, such as a pipe. Far side and near side electric pulses (waves) are transmitted into a magnetically permeable pipe at spaced locations to travel toward one another. These are synchronized to intersect at various locations on the pipe. The resulting wave forms are analyzed by combining adjacent wave forms resulting from pulses intersection at spaced locations. Two combined wave forms are analyzed by subtracting one from the other to produce a difference wave form and the difference wave forms are compared to detect corrosion.

38 Claims, 13 Drawing Sheets

FIG. 8A  FIG. 9A 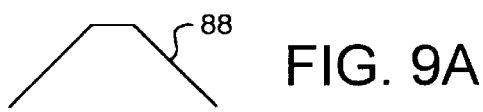
FIG. 8B  FIG. 9B 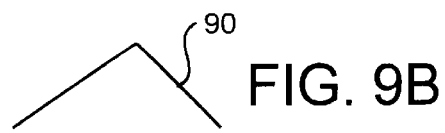
FIG. 8C  FIG. 9C 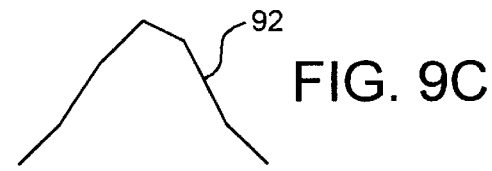
FIG. 8D 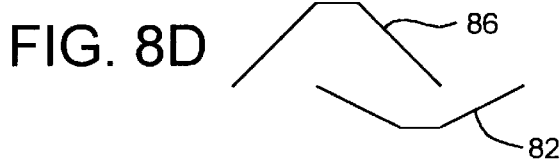 FIG. 9D 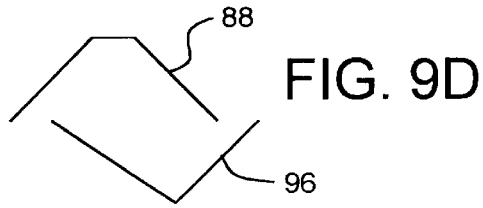
FIG. 8E 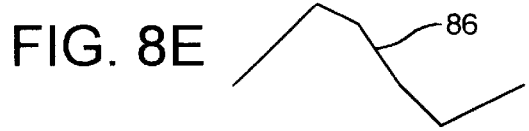 FIG. 9E 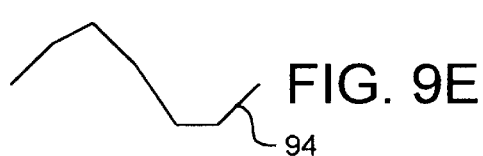
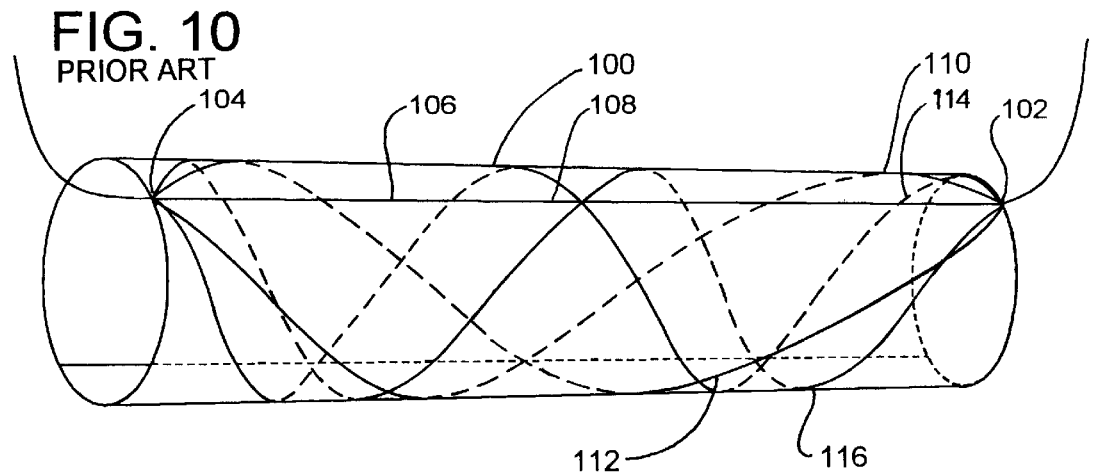
FIG. 10
PRIOR ART

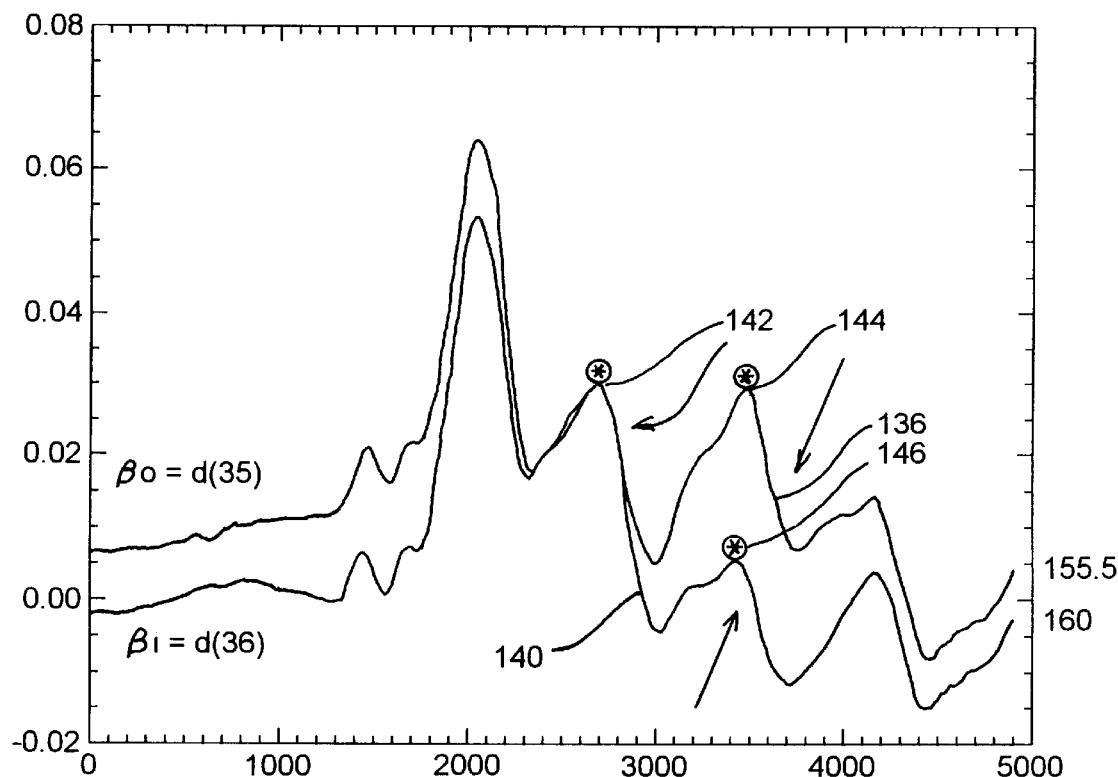
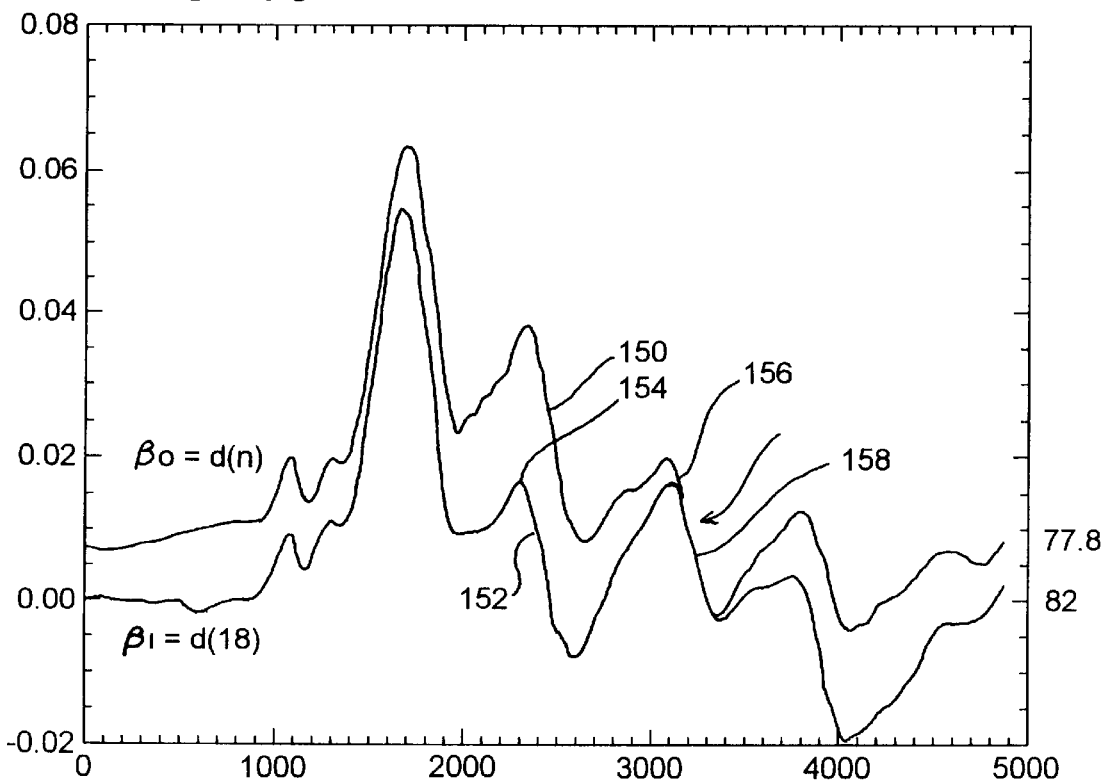

188

190

METHOD OF DETECTING CORROSION IN PIPELINES AND THE LIKE BY COMPARATIVE PULSE PROPAGATION ANALYSIS

BACKGROUND OF THE INVENTION a) Field of the Invention

The present invention relates to a system, apparatus and method for testing elongate objects, such as pipe, and is directed toward the problem of detecting corrosion, defects or other anomalies to the pipe under conditions where access and/or visual inspection of the pipe is either not possible or impractical.

b) Background Art

In petroleum processing and petrochemical plants and other industrial environments, it is common to have numerous pipes extending between various locations in the plant, with these pipes carrying fluid or gas (e.g. petroleum products), often under high heat and pressure. These pipes are commonly made of steel, and can have an inside diameter ranging anywhere from two to sixty inches, or even outside of this range. The exterior of these pipes are often insulated, with the insulating layers being as great as approximately ⅛ to 5 inches in thickness, or outside of this range.

For a number of reason, (safety, environmental considerations, avoiding costly shut-downs, etc.), the integrity of these pipes must be maintained. Defects in the pipe can occur for a number of reasons. One is that moisture can collect between the insulating layer and the pipe, thus causing corrosion (i.e. rust). Visual inspection of the steel pipe that is encapsulated in insulation is not possible unless the layers of insulation are removed, and then replaced. However, this is expensive and time consuming, and as a practical matter it would be economically unfeasible to accomplish the inspections with reasonable frequency.

It is the object of the present invention to provide a means of inspecting pipes under the circumstances given above in a manner that corrosion, other defects and/or anomalies can be detected with a relatively high degree of reliability, and in a manner that the various difficulties of inspection, such as those mentioned above, can be diminished and/or alleviated.

SUMMARY OF THE INVENTION

The method of the present invention enables corrosion on an elecromagnetical permeable elongate member, such has a pipe, to be detected quite effectively. More specifically, this method enables much of the irrelevant information (reflections, electromagnetic noise) to be elimiated from the wave form, and then the wave forms processed in a particular manner to enable clearer identification of variations in the wave form that would indicate corrosion.

In the method of the present invention, a nearside and far side electric or electromagnetic pulses (waves) are transmitted from, respectively, nearside and farside spaced transmitting locations on the elongate member. The pulses (waves) travel toward one another to intersect at intersecting locations on the elongate member.

The farside pulses are received as wave forms at a receiving location after intersection with related nearside pulses. The transmission of the nearside and farside pulses are synchronized so that the intersections of the near side and far side pulses (waves) occur at spaced intersecting locations on the elongate member.

The wave forms of at least two of the far side pulses (waves) which are spaced from one another are combined to form a composite wave form. A variation of variations are ascertained from the composite wave form as a means of detecting corrosion.

In the preferred form, one of the wave forms of the two wave forms that are to be combined is inverted and then added to the other of the waveforms being combined to create a difference waveform, and variations in the difference wave form are ascertained as a means of detecting corrosion.

Also, in the preferred form, the nearside pulses which pass through points of intersection that are adjacent to one another are considered to be sequential nearside pulses, with the order of sequence being the same as the order in which the points of intersection are spaced along the elongate member. The combining of the nearside waveforms is accomplished in a pattern such that first and second adjacent wave forms are combined to make a first composite waveform, the second waveform and an adjacent third waveform are combined to make a second composite waveform, the third waveform is combined with an adjacent fourth waveform to make a third composite waveform, with the pattern repeating itself with subsequent pairs of waveforms from adjacent farside pulses. Adjacent composite wave forms are compared with another as a means of detecting corrosion.

A reference wave form is established by creating composite wave forms resulting from pulses that intersect at non-corroded areas of the elongate member, and identifying composite waveforms that differ from the reference composite waveform by a phase shift and/or dispersion and/or amplitute and and/or wave distortion.

Corrosion that is present between two adjacent points of intersection on the elongate member is detected by comparing a composite wave form resulting from combining the difference waveform overlapping the point of intersection with difference wave forms on opposite sides of the overlapping composite waveform.

Also, corrosion that is present at a point of intersection of two wave forms can be detected by deriving two difference waveforms by combining the waveform at the point of corrosion with adjacent waveforms to form two difference wave forms which are then compared.

Also, two additional difference wave forms that are on opposite sides of, and adjacent to, the two difference waveforms which are analyzed to detect the corrosion are compared with the two difference waveforms which are combined at the point of intersection as a means of detecting corrosion.

Other features of the present invention would become apparent from the following detailed description.

BRIEF DESCRIPTION OF THE DRAWINGS

FIG. 2 is a graph illustrating one way in which data can be taken and presented in accordance with the present invention, this graph plotting propagation time against distance from A to B and again from B to A giving a reversed profile;

FIGS. 8A through 8E and FIGS. 9A through 9E are two series of Figures similar to those of FIGS. 7A through 7E, and to illustrate further the certain principles of difference wave forms;

FIG. 10 is an illustration of the paths of the electromagnetic wave components traveling along a section of pipe; and FIGS. 11–16 are presentations of wave forms illustrating the difference wave forms produced in accordance with the method of the present invention.

DESCRIPTION OF THE PREFERRED EMBODIMENTS

Figure 1:
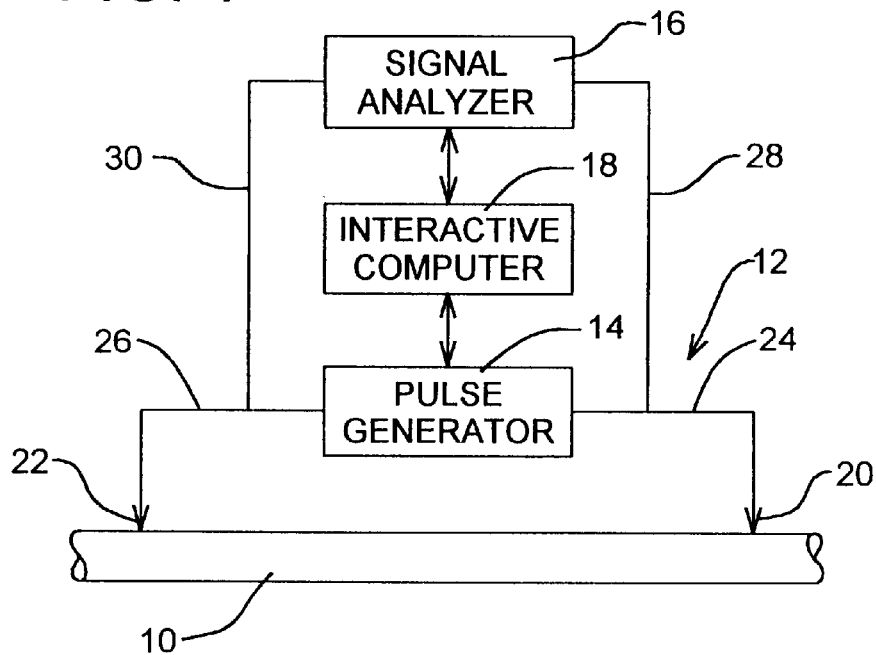
FIG. 1 is a somewhat schematic view of the system of the present invention being in its operative position where it is being used in testing a length of insulated pipe.

The basic testing apparatus and method of the present invention will now be described with reference to FIG. 1. There is shown a pipe 10 having a section 11 which is under test. This pipe 10 is or may be a pipe or pipeline that would typically be used in the petroleum or petrochemical industry, where the pipe is made of steel and surrounded by a coat or layer of insulation.

The apparatus 12 of the present invention is shown somewhat schematically in its operating position, testing the section 11 of the pipe 10. This apparatus 12 comprises a pulse generator 14, a signal analyzer 16, an interactive computer 18, and two transmitting/receiving antennas 20 and 22. There are two cables 24 and 26 (or other signal or pulse transmitting means) interconnecting the antennas 20 and 22, respectively, to the pulse generator 14. There is a second pair of cables or other transmitting means 28 and 30 connected between the cables 24 and 26, respectively, and to the signal analyzer 16.

When the transmitted pulse is received by one or the other of the antennas 20 or 22, this pulse is in turn transmitted to the signal analyzer. Certain analysis can immediately take place in the signal analyzer 16. Alternatively, the information relating to the pulse can be stored and analyzed at a later time. The computer performs certain control functions in the proper transmission and reception of the pulses and other functions.

There are several ways in which an apparatus, such as the apparatus 12, can be used in detecting corrosion in pipes, and two of these will be discussed below.

There is a first method where a single pulse is transmitted from the pulse generator 16 to one or the other of the antennas 20 or 22 to cause the wave form to travel from the location of that antenna 20 or 22 along the pipe 10 to the location of the other antenna 20 or 22 where the signal from the wave form is received. The distance between the sending location 20 and the receiving location 22 is ascertained accurately, and the timing of the time of transmission of the pulse from the antenna 20 or 22 to the other antenna 20 or 22 is measured very accurately (desirably to a fraction of a nanosecond or even to a very small fraction of a nanosecond). If the section between the two test locations 20 and 22 is non-corroded, and if the pipe is uniform along its length, then the pulse will arrive at the receiving location 22 in a wave form which is in the same general pattern (except possibly for disturbances, such as a near by magnetic field, electromagnetic noise, etc.). Also, the rate of travel of the pulse would remain substantially constant, provided the pipe remains uncorroded and uniform.

However, when corrosion is encountered between the points 20 and 22, the corrosion will affect the wave form by retarding its velocity diminishing its amplitude, and also possibly changing the actual wave form itself.

One method of utilizing this technique is to send the pulse from the transmitting location to the receiving location over an uncorroded section of pipe of a know length and diameter, and known characteristics, relative to its transmission of electromagnetic waves. This would establish the time of travel of the wave from the transmitting to receiving location and the expected configuration of the wave form at the receiving location.

Then various sections of the pipe are tested, as illustrated in FIG. 1. When there is a delay in the predicted arrival time of the wave form and/or deviations from the reference wave form for uncorroded pipe, then this will presumed to be due to corrosion on the pipe. However, it should also be understood that some other disturbance (e.g. nearby electromagnetic noise, presence of some other object that would disturb the electromagnetic field) could also affect the wave form, and this should be accounted for.

The second method which will be discussed further in this text is what is termed the "dual pulse" method, described in U.S. Pat. No. 4,970,467. In this method, the same apparatus as shown in FIG. 1 can be used. However, instead of using a single pulse or series of single pulses, as in the method described above, both antennas 20 and 22 are used as both transmitting and receiving antennas in the same timeframe. Thus, as one pulse is transmitted from the antenna 20, one is also transmitted from the antenna 22. These pulses travel toward one another and "collide" at some intermediate location along the pipe. This meeting of the pulses will cause variations in both of the wave forms as they move through the area of collision toward the other antenna which is its receiving location.

By properly coordinating the precise time at which the pulses are transmitted from the two locations 20 and 22, the point of collision along the length of the pipe can be caused to occur at any desired location along the length of the pipe. Then by changing the relative time transmissions of the pulses in small increments, this point of collision can be stepped along the length of the pipe.

As described in the above noted patent, when the point of collision occurs at a location where there is corrosion, the wave form resulting from the collision will be different from a reference wave form which would occur where the collision point is at a non-corroded section of pipe. Thus, not only is there a means of detecting corrosion, but also a means of determining the location of such corrosion.

Also, the antennas 20 and 22 could be used only as transmitting antennas and two additional antennas could be used as receiving antennas. Further, other transmitting and receiving devices could be used, such as by making a direct electrical connection to the pipe.

The present invention is particularly adapted for extracting information from the wave forms resulting from the dual pulse method described above.

A first embodiment of the method of the present invention is described in the following text, with reference to FIGS. 2A–2B through FIGS. 9A–9E. A second embodiment is also disclosed later herein, using in part the same principles as the first embodiment, and this will be described later with reference to FIGS. 10–16.

Figure 2A:
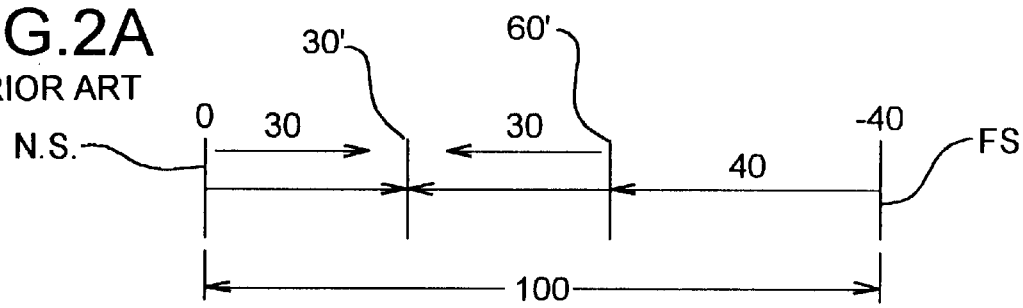
FIGS. 2A and 2B are schematic drawings showing the intersection of two pair of pulses at adjacent spaced locations.
Figure 2B:
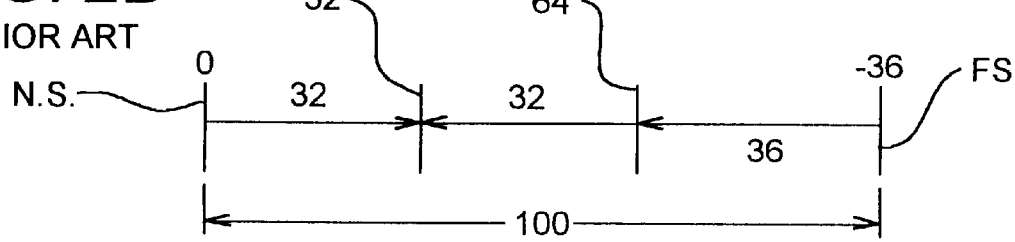

Reference is first made to FIGS. 2A and 2B which are schematic illustrations of the operation of the dual pulse method. In FIG. 2A, there is schematically shown a one hundred foot length of pipe. It will be assumed that the pulse travels along the length of the uncorroded pipe at the rate of one foot per nanosecond.

In FIG. 2A, the near side pulse is transmitted into the pipe at the location NS (near side location) at a point in time indicated at zero. The second pulse is transmitted into the pipe at the far side location (designated FS), and in this particular example, it is assumed that the second far side pulse is transmitted into the pipe forty nanoseconds earlier than the time the near side pulse is transmitted into the NS location.

Therefore, it can be seen that when the far side pulse has traveled along the length of the pipe for forty nanoseconds to reach a location indicated at the sixty foot location, the near side pulse is transmitted at time zero from the near side location.

The near side and the far side pulses travel toward one another, each traveling thirty feet until they intersect at the thirty foot location on the one hundred foot pipe. At the intersection, the two pulses interact with one another, and the far side pulse continues it path of travel to the near side (NS) location. Also, the near side pulse after passing through the point of intersection continues its course of travel toward the far side (FS) location.

At this time, it is important to note that each of the pulses is a somewhat complex wave form. First, as a wave form travels along the length of the pipe, it is subject to attenuation, distortion, interference and dispersion. Further, each wave can be considered as having what we might term wave components made up of earlier and later arrivals. There is a first arrival which will travel the shortest course from the transmitting to the receiving location. Thus, if both the transmitter and the receiver are on top of the pipe, the first arrival will travel along the top surface of the pipe in a straight line. Then there are second arrivals which are pulse components which follow a helical path once around the pipe to arrive at a short time later. Then there are third, fourth, fifth, . . . etc. arrivals which come at yet later times. Further, there are quite commonly outside sources of interference, such as sources of electromagnetic radiation, nearby objects which may interact with the wave form traveling along the pipe, and thus become activated and in turn transmit their own electromagnetic radiation back into the pipe under test. Further, there are reflections and refractions.

To return to FIG. 2A, let us first assume that the one hundred foot section of pipe which is under test is free of corrosion. After the near side and far side pulses intersect at the thirty foot location, there is a resulting wave form which reaches the near side receiving location, which is the composite of both the original near side pulse and the far side pulse, with these having been modified or affected to some extent by reason of intersecting.

It has been found that if the intersection of the near side and far side pulses takes place at a location on a pipe which is noncorroded, then the resulting pulse which travels through the location of intersection will have certain characteristics typical of a situation where the intersection takes place at a non-corroded area of pipe. However, if the intersection of the near side and far side pulses take place at a location where there is corrosion, the two pulses interact in a rather different manner, and the resulting wave form of each of the intersected pulses has different characteristics.

However, the analysis of the wave form as a means of detecting corrosion is difficult to quantify. There are features such as rise time, slope, amplitude, and phase change, all of these being relevant characteristic of the wave form.

Figure 3:
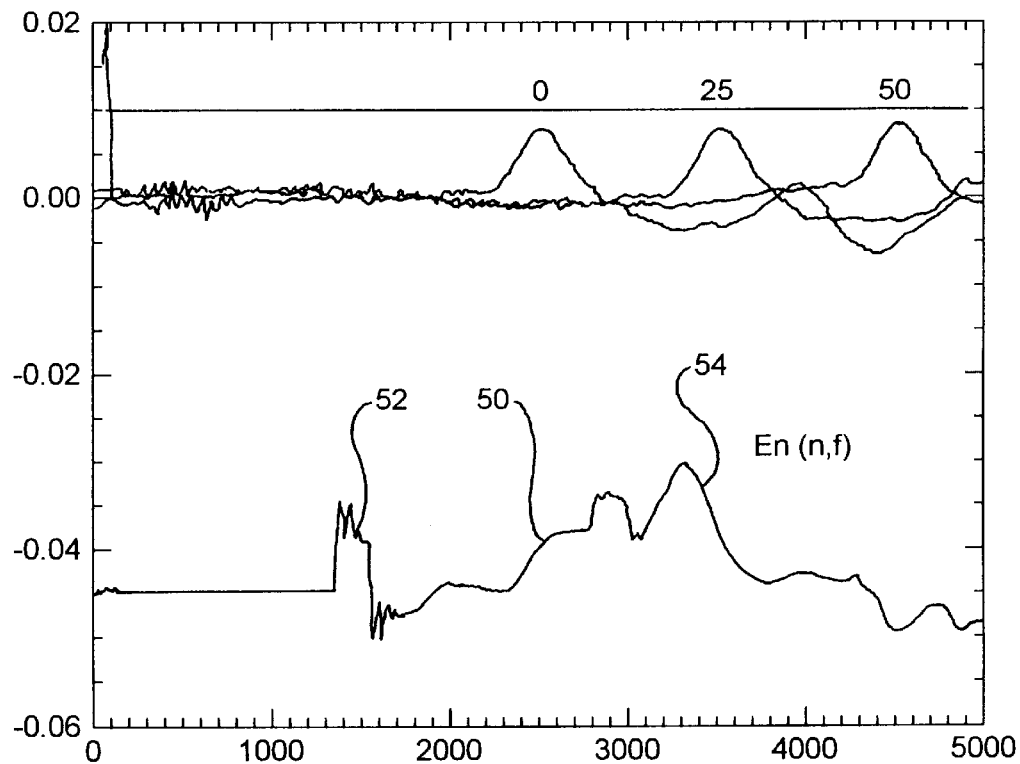
FIG. 3 is a graph which displays a curve in the lower part of the graph which represents a composite wave form resulting from both the near side of far side pulses traveling along the pipe section under test, and the curves at the upper part of FIG. 3 showing resulting wave forms at different locations, using the method of the present invention.

To illustrate this, reference is made to the lower curve shown in FIG. 3. This curve, designated 50, is a composite curve which results from the combination of both the near side and the far side pulses. In this instance, one transmission takes place at the near side, and the receiving antennae is also located at the near side. The portion of the curve indicated at 52 represents the near side pulse being transmitted into the pipe at the transmitting location.

The portion of the curve indicated at the general area of 54 represents a portion of the composite wave that arrives at the near side receiving location, this being a combination of the far side wave and near side wave components. As indicated above, there are reflections, refractions, late arrivals, etc., which complicate the wave form.

Reference is now made to FIG. 2B, which shows a second dual pulse operation where the transmission time of the far side pulse has been delayed by four nanoseconds, so that it is transmitted thirty six nanoseconds before the transmission of the near side pulse. It can be seen that after the far side pulse has traveled thirty six feet, the transmission of the near side pulse takes place. Thus when the near side pulse is transmitted, the far side pulse is at the sixty four foot location, and the two pulses intersect at the thirty two foot location.

With the foregoing being presented, the method of the present invention will now be described. Let us assume that the dual pulse testing method is being accomplished and that the near side and far side pulses are timed (as indicated in FIG. 2A) so that there is intersection at the thirty foot location on the one hundred foot pipe. Let it further be assumed that the wave form which is received at the near side location looks the same, or similar to, that shown in the bottom part of FIG. 3.

Now let us assume that a second testing operation is to be initiated and the far side pulse is delayed by four nanoseconds. However, the transmission at the near side location remains constant, in terms of time, and is still transmitted at zero time. As illustrated in FIG. 2B, the intersection takes place at the thirty two foot location. What this would effectively mean is that the portion of the composite curve which is attributable to the far side pulse would have been delayed, relative to the time of transmission of the near side pulse, and that, with reference to the lower curve of FIG. 3, the portion of the composite wave form contributed by the far side pulse would have shifted to the right somewhat, from what is shown in the lower curve of the graph of FIG. 3.

In order to extract meaningful information about the condition of the pipe, the following is done. First, the composite wave form which results from the transmission and intersection of pulses as shown in FIG. 2A is stored in the memory. Next, the second composite wave form resulting from the transmission of the near side and far side pulses in accordance with FIG. 2B is also received. Then the second composite wave form resulting from the test operation of FIG. B is subtracted from the composite wave resulting from the test operation in FIG. 2A.

At this point, it is very important to keep in mind that the near side pulse has in both instances (in the operation of FIG. 2A and the operation of FIG. 2B) been transmitted at zero time. Thus, in both the FIG. 2A and FIG. 2B operation, the near side pulse has not changed position. From this, it becomes apparent that the contribution of the near side pulse to the composite wave form is essentially subtracted out of the composite wave form resulting from the operation of FIG. 2A. Now, let us turn our attention to the far side pulses of the test operation of FIG. 2A and FIG. 2B. With the far side pulse having been delayed by four nanoseconds, the wave component of the far side pulse has now shifted from the first location in the first operation of FIG. 2A four nanoseconds to a second position composite curve of the second test operation of FIG. 2B.

With the entire first composite curve being subtracted from the entire second composite curve, there remains what can be termed a "difference wave form". It has been found that if in the two dual pulse operations where the intersecting locations are stepped within a reasonably close distance from one another, and if uncorroded pipe is encountered at both intersecting locations, the resultant difference wave form is a reasonably well defined and identifiable peak.

Reference is now made to FIG. 3. It can be seen that the curve in the upper part of FIG. 3 shows three separate peaks designated "zero", "twenty five", and "fifty", respectively. Each of these peaks is the result of using the method of the present invention where the point of intersection for the two adjacent dual pulse operations has been stepped by an interval of about 5 feet.

Figure 4:
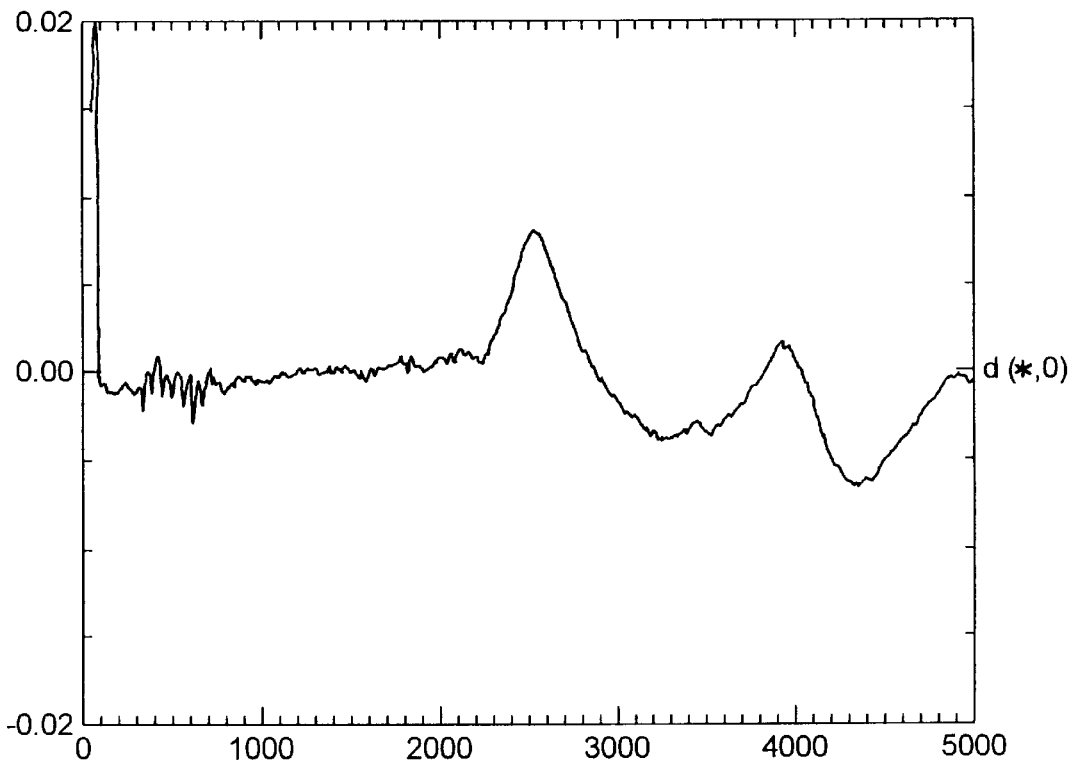
FIG. 4 is a graph which is similar to the upper part of the graph of FIG. 3, displaying separately a first resulting wave form identified at the zero location shown in FIG. 3.
Figure 5:
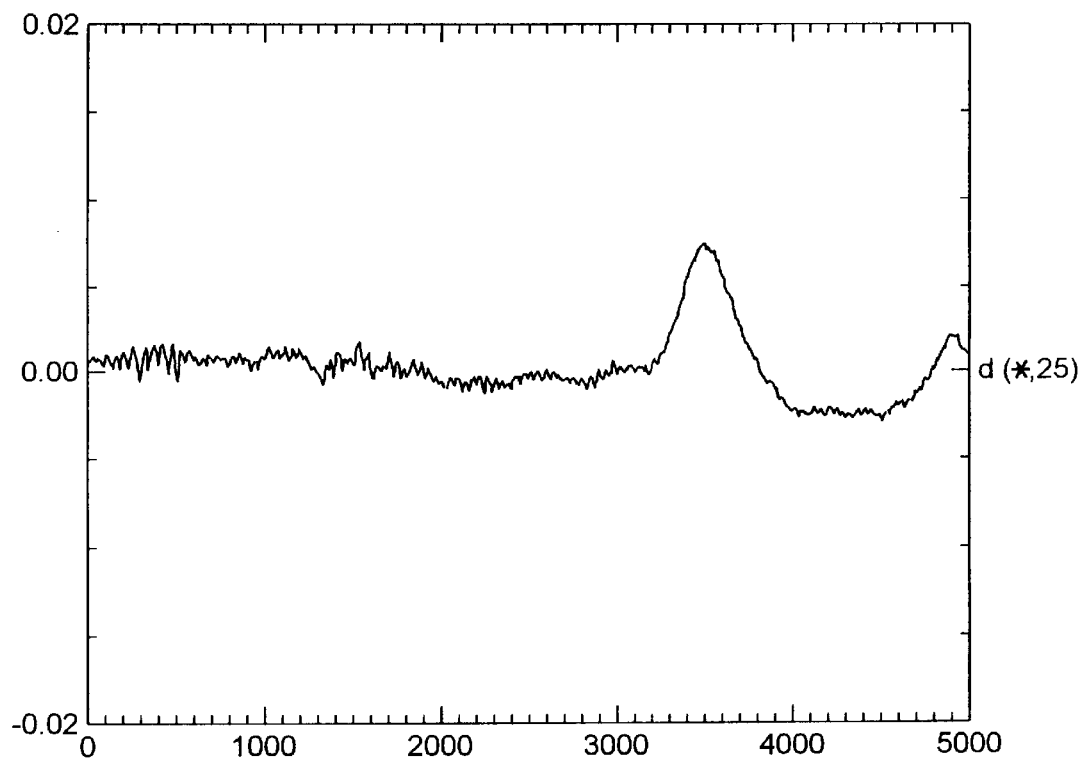
FIG. 5 is a graph similar to FIG. 4, but showing separately the resulting wave form identified at the 25 location shown in FIG. 3.
Figure 6:
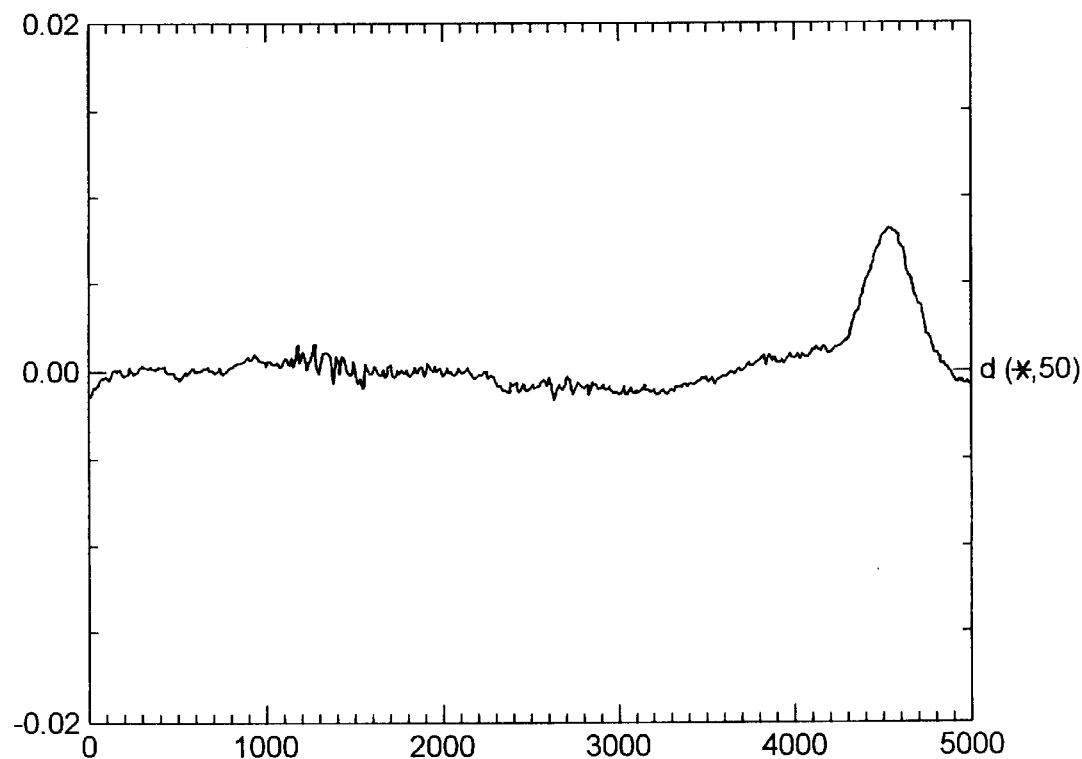
FIG. 6 is a graph similar to both FIGS. 4 and 5, but showing separately the resulting wave form at the 50 location of FIG. 3.

To provide cleaner representations of the wave forms, FIG. 4 illustrates the single curve indicated at "0" in FIG. 3; FIG. 5 illustrates only the curve indicated at "25" in FIG. 3; and FIG. 6 illustrates only the curve indicated at "50" in FIG. 3.

It should be noted that the wave forms indicated at "0", "25", and "50" in the top part of FIG. 3 are actual wave forms extracted from adjacent wave forms similar to the ones shown in the lower part of FIG. 3. It is important to note that if the composite wave form is not formatted correctly, the difference between adjacent wave forms does not provide the "effect" wave forms shown in FIG. 3.

To review how to format the data correctly, consider the two active wave forms on the pipe, one from the near side (NS), and the other from the far side (FS). When the data analyzer is synchronized with the near side pulse, the near side component of the composite pulse will not move (i.e. shift position). However, the FS (far side) pulse, which is synchronized to the master clock, will move across the screen from left to right and will modify the composite wave form for each intersection along the pipe. When the composite wave forms are subtracted from each other, two significant things happen:

1. The effect of the NS pulse, which has a very large amplitude with respect to the FS pulse, is cancelled, since this NS component in the composite wave form is fixed in time.
2. The resulting difference wave form represents the difference between the two adjacent FS pulses that have intersected with the NS pulses at two different points on the pipe.

When this difference occurs, then the "effect" (time rise, slope, amplitude, dispersion and absolute time, among many parameters that are effected by corrosion) influence the shape of the difference wave form. The difference wave form will be displaced in time with respect to other adjacent pairs. This time displacement is a good indication of the condition of the pipe, provided it can be meaningfully interpreted. The difference wave forms shown here are examples of the wave forms that are well defined, but are very difficult to extract real time information. (See FIGS. 4, 5 and 6. Note particularly FIG. 6 at the "knee" of the wave form is not well defined, and could be selected anywhere from a point near thirty two hundred to forty two hundred, a range of one hundred nanoseconds. Automating a selection of the absolute time location of the knee is very difficult and sometimes impossible. However, the peak is well defined. The peak is not just a voltage difference between two different response wave forms, but it is determined by the shape factors involved with the leading edge of the two adjacent wave forms.

For example, if the two adjacent wave forms are displaced more in time than any two other adjacent wave forms, it will result in an increase of amplitude. Hence, "Δ" (peak) is a function of time. It is also a function of actual amplitude different between two different wave forms. Also, if the leading edge of one wave form is distorted as a result of corrosion, this distortion will result in a change of amplitude in the difference wave form and a shift in the position of the peak with respect of time. When the pipe is very good, the peak is very sharp and the shape of the difference wave forms extremely uniform. When the pipe has anomalies (e.g. corrosion), the shape of the difference wave form is significantly altered and the corrosion effect (CE) displaced by major differences in the leading edge. These differences result in an effective peak shift that can be related directly to pipeline quality.

This peak shift is much easier to instrument and measure than other parameters. Also this peak shift is an indicator of the cumulative effect of all individual parameters and effect the electromagnetic response, even if they might be very difficult to measure individually. As the pipe degrades, the peak distorts more readily because of the complex contribution of all driving forces. In a perfect system, every difference pulse should be identical. Hence, measuring the time associated with the first peak occurring after an indefinite knee of a differential pair, provides an effective way of extracting critical information and measuring the corrosion effect.

Obviously, a stable source is required and is being used for this system. From the wave forms included, it should be obvious that measuring the peak is easier than measuring the time related to the knee. When the peak is not well defined, it will indicate different anomalies on the pipe. The process of measuring the corrosion effect is designed to impose the quality of data and reduce the time required to collect and analyze the data in the field.

Figure 7A:
FIGS. 7A through 7I are a series of simplified illustrations of wave forms to demonstrate certain principles of different wave forms.
Figure 7B:
Figure 7C:
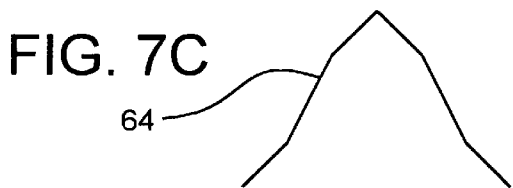
Figure 7D:
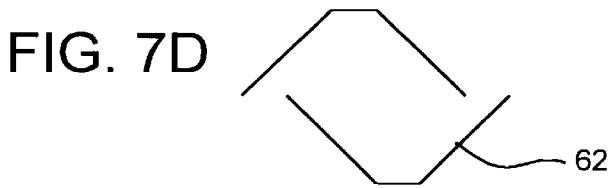
Figure 7E:
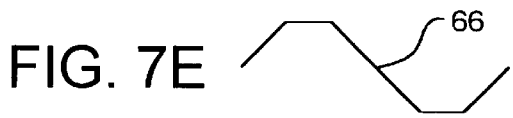
Figure 7F:
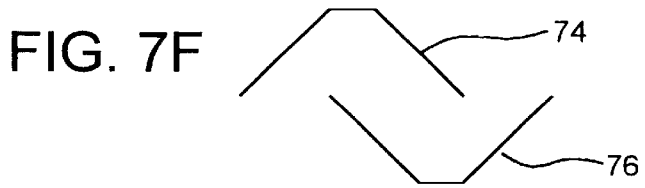
Figure 7G:
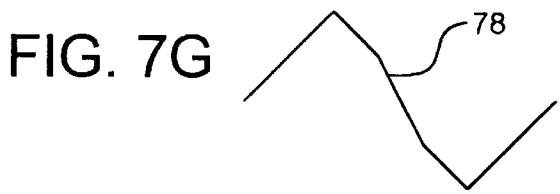
Figure 7H:
Figure 7I:
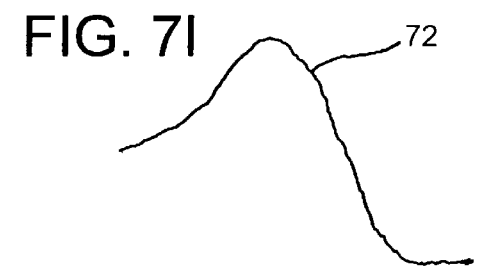

To illustrate in a rather simplified fashion certain aspects of the present invention, relative to subtraction of one wave form from another, reference is now made to FIGS. 7A through 7G, and also FIGS. 7H and 7I.

FIG. 7A shows a rather simple wave form 60 which is drawn, for convenience, in straight lines. FIG. 7B shows the same wave form at 62, but offset one unit from the wave form 60. FIG. 7C shows the summation of the wave forms 60 and 62 as the wave form 64. It is possible to drive meaningful information from the wave form in FIG. 7C where the wave invert forms are added, but it is preferred to first one of the wave forms and then add the two together. This is done in FIG. 7D which shows the wave form 60, with the offset wave form 62 inverted, and the summation of the wave 60 and the inverted wave 62 accomplishes a subtraction of the wave forms of FIG. 7A and 7B. This results in the difference in the difference wave form 66 shown in FIG. E.

As indicated above, these curves are somewhat artificial, and in actuality, these simple wave forms would not be formed with these straight lines. Rather FIGS. 7H and 7I would be more realistic, where we see the wave form 68 and a very similar wave form 70 offset in the wave form 68. In 7I, there is shown a difference wave form 72 which would result from subtracting the wave 70 from the wave form 68. It can be seen that the difference wave form 72 forms in a rather well defined peak.

For purposes of further analysis, in FIG. 7F, the wave form 74 is shown, exactly in the same form and position as the wave form 60 of FIG. 7A. Then the same wave form is shown in FIG. 7F at 76, inverted and shifted two units from the wave form 74. Then when the wave form 76 is subtracted from the wave form 74, there is the difference wave form 78 shown in FIG. 7G. It will be noted that with the wave form 76, spaced two units away from the wave form 74 (instead of one unit, as in FIGS. 7A and 7B) has an amplitude which is twice the amplitude of the difference wave form 66. This illustrates that if the time displacement of the wave forms increases, the amplitude of the difference wave form would be expected to increase. This is simply by way of illustration, and relates to only one particular facet of detecting corrosion from the difference wave form.

For purposes of further analysis, reference is made to FIG. 8A through 8E and to FIGS. 9A through 9E.

In FIG. 8A, there is shown a wave form 80, and in FIG. 8B a second advanced wave form 82 which has been attenuated and delayed, presumably because of encountering corrosion in the pipe. FIG. 8C shows the summation of these, this being the wave form 84. FIG. 8D shows the same wave form 80 and the adjacent wave form 82 inverted. FIG. 8E shows a difference wave form 86 which results by subtracting the wave form 82 of FIG. 8B from the wave form 80 of FIG. 8A.

In FIG. 9A, these same steps are followed. FIG. 9A shows a wave form 88 which is the same as the wave form 80 of FIG. 8A. FIG. 9B shows a second wave form 90 delayed by one unit, and having a different slope along the leading edge. FIG. 9C shows the summation wave form at 92. FIG. 9D shows the wave form 88 and the second wave form 90 inverted. FIG. 9E shows the difference wave form at 94.

In reviewing FIGS. 7A through 7I, FIGS. 8A through 8E, and also FIGS. 9A through 9E, four of the figures show difference wave forms, these being the difference wave form 66 in FIG. 7E, the difference wave form 78 in FIG. 7G, the difference wave form 86 in FIG. 8E, and the difference wave form 94 FIG. 9E. It can be seen that the different characteristics of these difference wave forms emphasize the difference between the adjacent wave forms.

It should be kept in mind that these wave forms of FIGS. 7A–7I, 8A–8E and 9A–9E are not the more complex composite wave forms such as shown at 50. These are simplified wave forms provided simply to show some of the principles involved.

What the method of the present invention accomplished is the elimination of a great deal of the irrelevant information. There is the tendency of the near side pulse to swamp out the far side pulse, mainly because the near side pulse has a substantially larger amplitude, since it is closer to the transmitting location. The components of the near side pulses are substantially eliminated. Beyond this, by subtracting the shifted wave components attributable to the far side pulses from one another is that a difference comparison is provided. If the pipe is substantially uniform along its length (non-corroded), and if the intersecting point of the pulses is stepped in even increments along the pipe, then the same or very similar difference waves are expected to be obtained. As indicated previously, the difference curves shown in the upper part of FIG. 3 are quite similar, indicating no corrosion or possibly minimal corrosion. Thus, the difference curves as shown in FIGS. 4 through 6 provide the meaningful information, without being cluttered by extraneous wave components.

A second embodiment of the present invention will now be described relative to FIGS. 10 through 16. By way of introduction, much of the focus on the analysis of the wave forms to detect corrosion has been directed toward the leading edge of the wave form or at least the early arrival portion of the wave form. To some extent, it has been recognized (or at least conjectured) that valuable information would be contained in the later arriving portions of the wave form. However, the problem is how such information could be identified and/or extracted.

As indicated earlier in this text, the propagating wave form can be considered to be a composite of a number of wave components made up at least in part of early and late arrivals. To illustrate this graphically, reference is made to FIG. 10 which shows a relatively short section of pipe, where there is a transmitting location 102 and receiving location 104. In this instance, these locations 102 and 104 are both at the top of the pipe and aligned. The straight line lengthwise axis between the points 102 and 104 is indicated at 106. Since this axis 106 is the shortest path between the points 102 and 104, the first arrival path would be along the path indicated at 108, which is coincident with the axis 106.

In addition to the first arrival wave component 108, there are two second arrival wave components, the travel paths of which are indicated at 110 and 112. It can be seen that each of these are helical paths, which travel longitudinally and through a helical curve of 360°. Then the third arrivals are indicated at 114 and 116, and these also are helical paths, but with a total circumferential component of travel of 720°.

Obviously, the second arrival has a longer path of travel than the first arrival, the third arrival has a yet longer path of travel than the second arrival, etc. If there is corrosion on the pipe, at least some of these later arrival pulse components will pass through the area or areas of corrosion and that path component will be delayed, attenuated, and/or otherwise modified.

Figure 11:
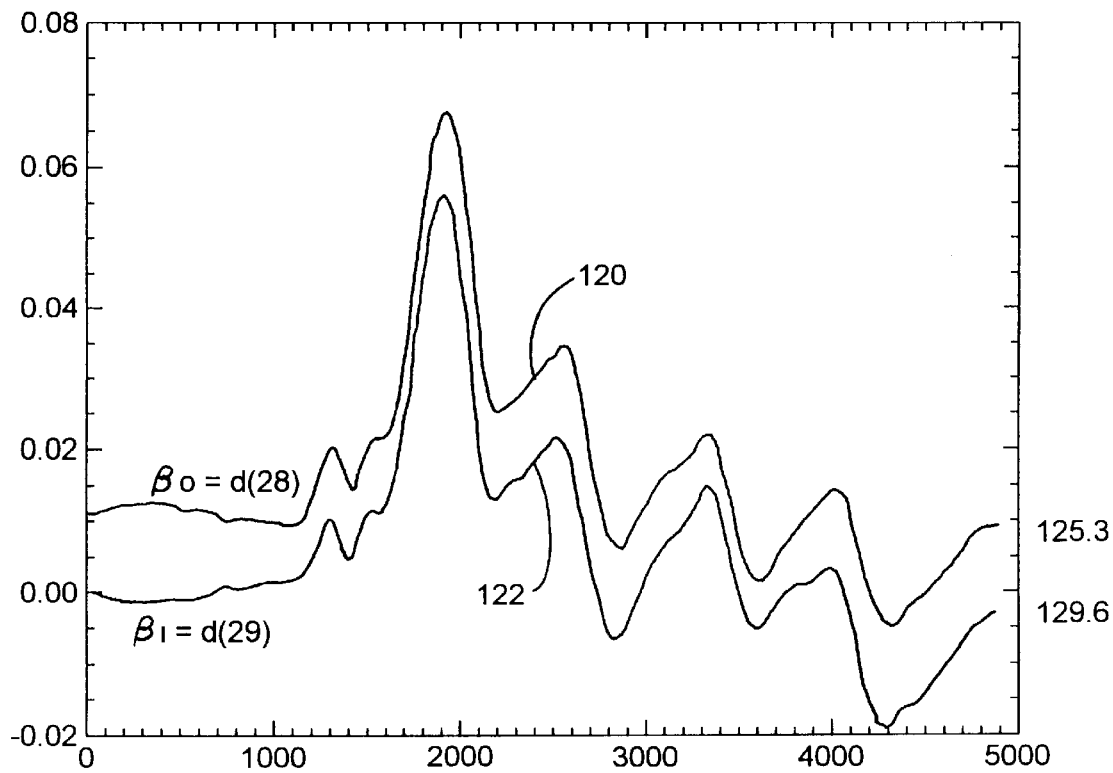

With the foregoing being given as background information, reference is now made to FIG. 11, which illustrates the wave forms obtained by the second embodiment of the present invention. In FIG. 11, the vertical axis represents voltage (measured in volts), and the horizontal axis measures time, with each increment representing ten nanoseconds. Thus, the numeral one thousand actually represents one hundred nanoseconds, the numeral two thousand represents two hundred nanoseconds, etc. It can be seen that the wave forms presented in FIG. 11 extend over a full five hundred nanoseconds.

The particular tests from which these curves were developed were done over a pipe section one hundred and sixty feet length (i.e. the transmitting location was one hundred and sixty feet away from the receiving location). Further, the dual pulse method was utilized, as indicated above. Since the entire pipe is encircled by electromagnetic energy, the effect of corrosion anywhere on the pipe will appear in the difference wave form obtained by intersection of the pulses at the location of corrosion.

The first steps in the second embodiment in the method of the present invention are substantially the same as those of the first embodiment. More specifically, a first testing operation was performed by transmitting the near side and far side pulse in timed relationship so that these would meet at a predetermined point of intersection. There is a composite wave form resulting from this first test operation and that is stored. Then, as described in the presentation of the first embodiment, there is a second operation in timing of the far side pulse so that it was either advanced or delayed so that the point of intersection was shifted, and the result was a composite wave being recorded that had components of the far side pulse shifted somewhat from the previous composite wave. As described in the first embodiment of this method of the present invention, one of the composite wave forms is subtracted from the other to get a difference wave form.

These steps are performed in the second embodiment of the present invention, and it will be recognized, of course, that these are substantially the same steps as described in the first embodiment. From this point on in the method of the second embodiment, a further analysis is conducted as will be described below.

For purposes of description, we shall consider the sequence of the difference wave forms and designate these as difference wave form 1, difference wave form 2, difference wave form 3, etc. It will be evident that the difference wave form 1 results from processing composite wave forms 1 and 2 which result from the first and second dual pulse test operations; difference wave form 2 is a result of processing the composite wave forms 2 and 3 resulting from the second and third dual pulse operations; etc.

In FIG. 11, there is first plotted the difference wave form 120, and this wave form is about five hundred nanoseconds in length. The next step is to plot the second difference wave form 122, but the second difference wave form 122 is shifted to the left, and is also lowered somewhat so that the second difference wave form 122 is aligned with and a short distance below, the first difference wave form 120. It will be observed in the wave form representation of FIG. 11 that the two wave forms 120 and 122 match each other rather closely. These two difference wave forms 120 and 122 were derived from adjacent composite wave forms, and both of these composite wave forms resulted from a dual pulse operation where the pulse is intersected at a noncorroded area (or at least a very lightly corroded area) of the pipe under test. As indicated at the right side of FIG. 11, the upper composite wave results from a difference wave form where a reference point of intersection was that at the 125.3 feet mark, while the second difference wave form 122 was made up of adjacent composite wave forms at a reference location 129.6.

Figure 12:
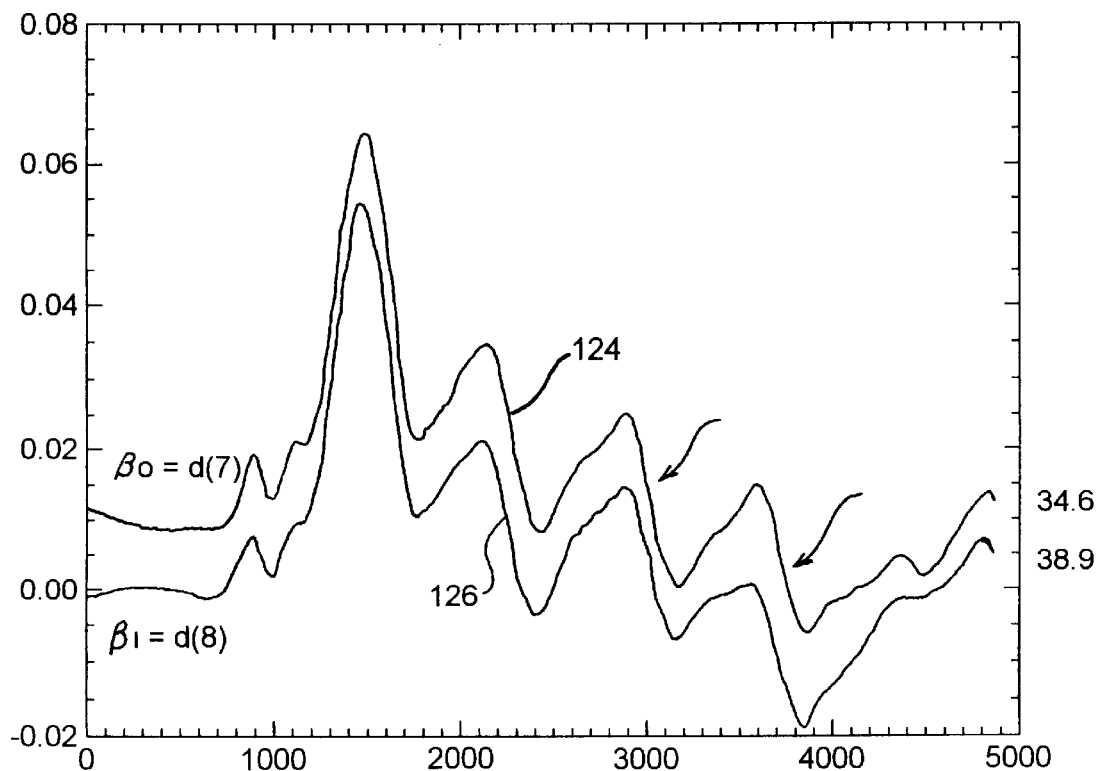

FIG. 12 shows two other reference wave forms 124 and 126, resulting from two adjacent pair of composite wave forms at reference locations at the 34.6 and 38.9 foot locations on the pipe section under test. These composite wave forms also resulted from the far side and near side pulses of each test operation intersecting at a noncorroded (or very lightly corroded) area of the pipe section under test.

Figure 13:
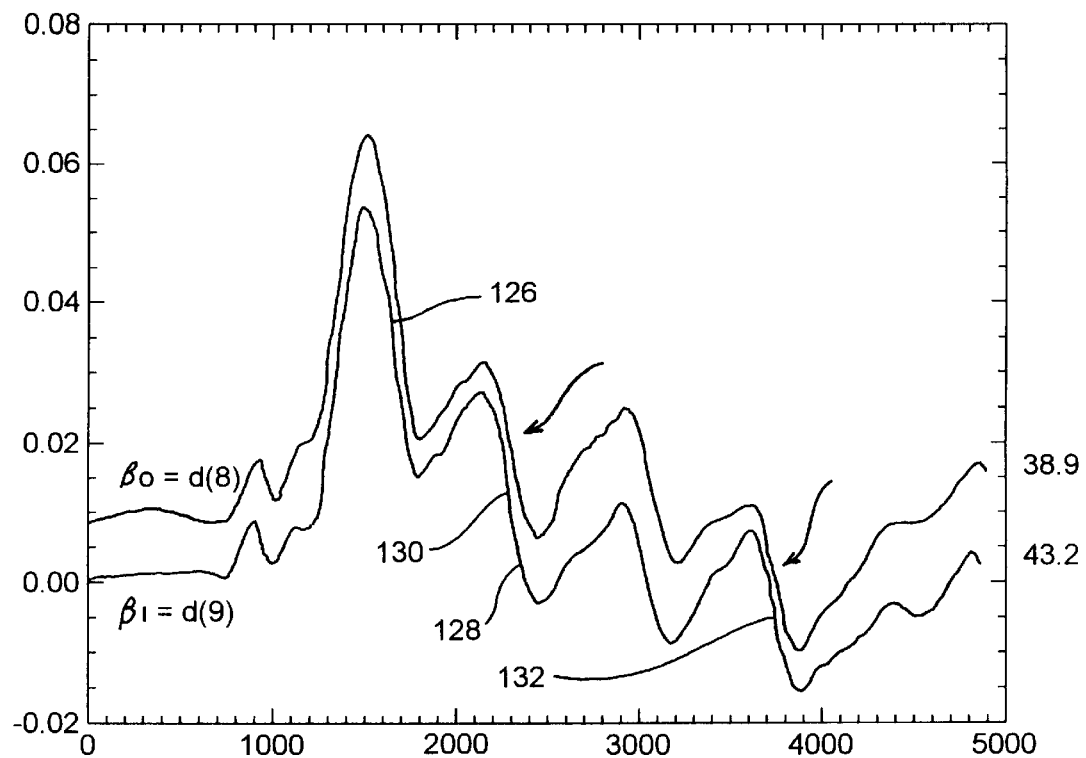

Reference is now made to FIG. 13, where there is shown as the upper wave form the same wave form 126, as shown in FIG. 12, this difference wave form having a reference location of 38.9 feet on the pipe. The lower wave form 128 has a reference of 43.2. This was at a somewhat corroded pipe section having a corrosion index of 1.0262. (The corrosion index is a scale which is utilized by the inventor in rating areas of corrosion. A rating of 1.000 would be no corrosion and the higher the number, the greater the severity of corrosion).

It will be noted in FIG. 13 that the lower wave form 128 has at two areas something of a phase shift, indicated at 130 and 132.

Figure 14:
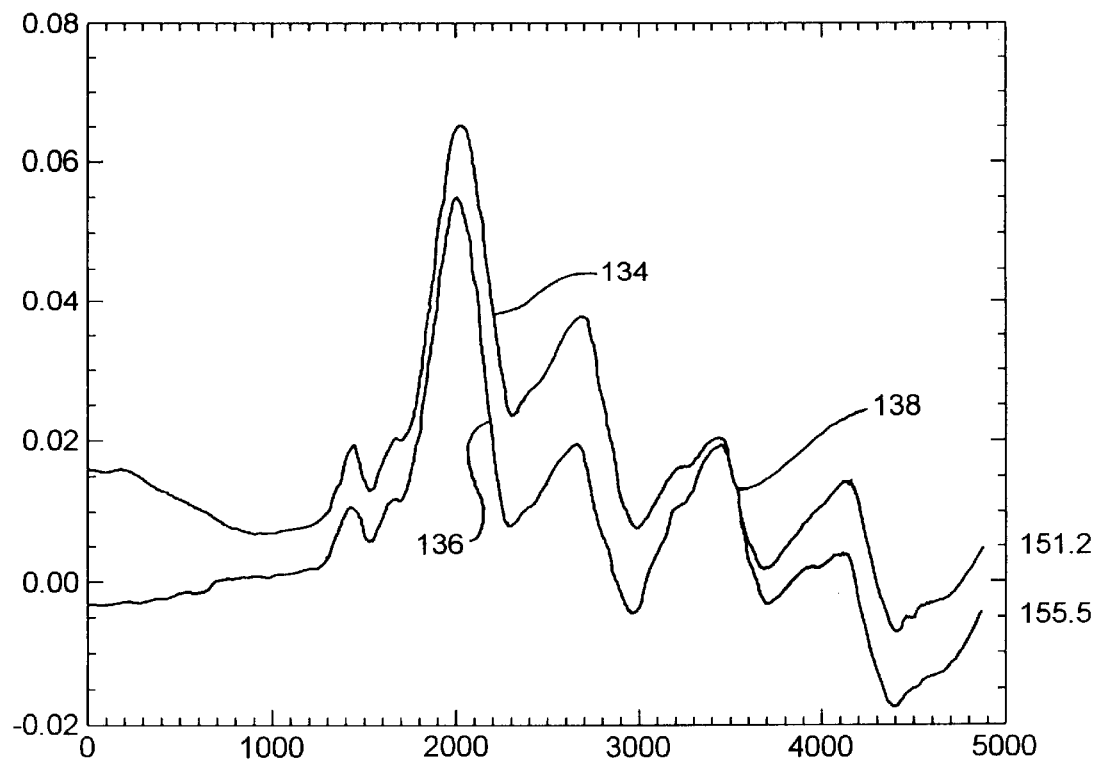

Reference is now made to FIG. 14, where there are two adjacent reference wave forms at locations along the pipe section at the 151.2 foot location and the 155.5 foot location. There was a corrosion index of 1.055, which is higher than in FIGS. 11, 12 and 13. These wave forms are indicated at 134 and 136. It can be seen that at the location 138 there is a rather substantial phase shift.

Next, attention is directed toward FIG. 15 which shows as the upper wave form the same wave form 136 which is the lower wave form in FIG. 14, and a new difference wave form 140 taken at a reference location of 160 feet on the pipe. These wave forms resulted from composite wave forms developed with the intersecting locations being at more highly corroded areas. Several features should be noted. In observing the peak location at 142, and the two peak locations at 144 and 146, it can be seen that there are substantial amplitude differences with regard to the second and third peaks between these curves 136 and 140. In addition there is significant phase shift indicative of corrosion anomalies.

It is enlightening to observe the difference curve 134 which is at the reference location 151.2 (FIG. 14) and the curve 140 which is at the reference location 160 (FIG. 15). It can be seen by matching up the curves 134 and 140 that these correspond fairly closely to one another, at least much more closely to one another than each matches up with the curve 136. This would indicate that the corrosion area is more likely in the area of the reference location 155.5, presumably somewhere between the 153 to the 158 area.

Finally, reference is made to FIG. 16, where there are two difference wave forms 150 and 152. It can be seen that the difference wave form 152 has substantial similarities to the curve 136 (see FIGS. 14 and 15). Further, it can be seen the match up between the wave forms 150 and 152 are rather similar to the matching of the wave forms of 134 and 136 in FIG. 14. More specifically, it can be seen that the second and third peaks 154 and 156, respectively, of the wave form 152 are of nearly equal amplitude, and then there is the phase shift at the area 158. This is a pattern quite similar to that shown at area 138 in FIG. 14.

Thus, it can be seen that with the method of the second embodiment of the present invention, the presence of corrosion is detected by a method which might be termed "whole wave analysis", which involves looking not only at the leading portion of the wave, but also a much greater time span of the wave form which also contains significant information. It also becomes apparent that valuable information is obtained from portions of the wave form as far along the wave form as two hundred to four hundred nanoseconds or longer from the first arrival of the electromagnetic pulse. Further, the location of the corrosion can be located within reasonably close tolerances by properly synchronizing the pulses so that the point of intersection is known.

Also, it should be noted that these readings were taken on the same section of pipe, but with the intersection being moved to different locations. Therefore, all of the wave forms developed for the data of FIGS. 11 through 16 passed over the same pipe section. The key difference is that the point of intersection was moved. When the point of intersection of the wave forms which were combined to make the difference wave forms were at an area of corrosion, the variations of the difference wave forms become apparent.

A third embodiment of the method of the present invention will now be described. In this third embodiment, as in the prior embodiments, the pulses will be transmitted from the far side and near side locations, and in this particular embodiment, the wave form which is to be analyzed to detect corrosion is the far side pulse arriving at a receiving location adjacent to the transmitting location at the near side. Also, in this third embodiment, the time intervals between the transmissions of the far side pulse will remain constant. Thus, to synchronize the pulses so that the point of intersection stepped along the length of the pipe, for each transmission, the near side pulses shall be advanced in timing by a short increment so that the point of intersection of the pulses will be stepped in a left to right direction across FIG. 18. In the first step of this further embodiment, the far side transmitter is shut down, and a series of pulses are transmitted from the near side and these are picked up by the near end receiving antenna that is closely adjacent to the near side transmitter. The timing of the transmission of the near side pulses is timed relative to a sender except that each subsequent transmission is advanced one additional increment of time, and in this particular example we will assume that it is being advanced by four nanoseconds for each pulse transmission.

Figure 19:
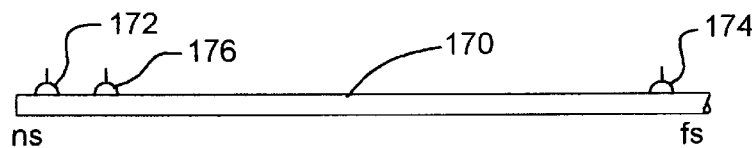
FIG. 19 is a schematic drawing of the place for the antennas in this third embodiment.

The first step in the method of this preferred embodiment will now be described with reference to FIGS. 17 and 19. In FIG. 19, there is shown a section of pipe 170 having a near side transmitting antenna 172 and a far side transmitting antenna 174. There is a receiving antenna 176 spaced from the transmitting antenna 172 a short distance toward the far side transmitting antenna 174.

Initially, the far side transmitter remains inactive so that the far side transmitting antenna 174 is not transmitting any signal. The near side transmitter is activated to transmit a series of timed pulses which are synchronized with regular time intervals. This is done in a manner that each subsequent pulse is advanced four nanoseconds relative to the preceding pulse.

For example, if the near side pulses are to be transmitted every two seconds, less the time of the advance of the timing, the first pulse would be sent at 0 seconds. The second pulse would be transmitted four nanoseconds before the two second interval. The third pulse would be sent eight nanoseconds sooner than the four second interval. The first pulse would be sent twelve nanoseconds before the six second interval, etc.

Figure 17:
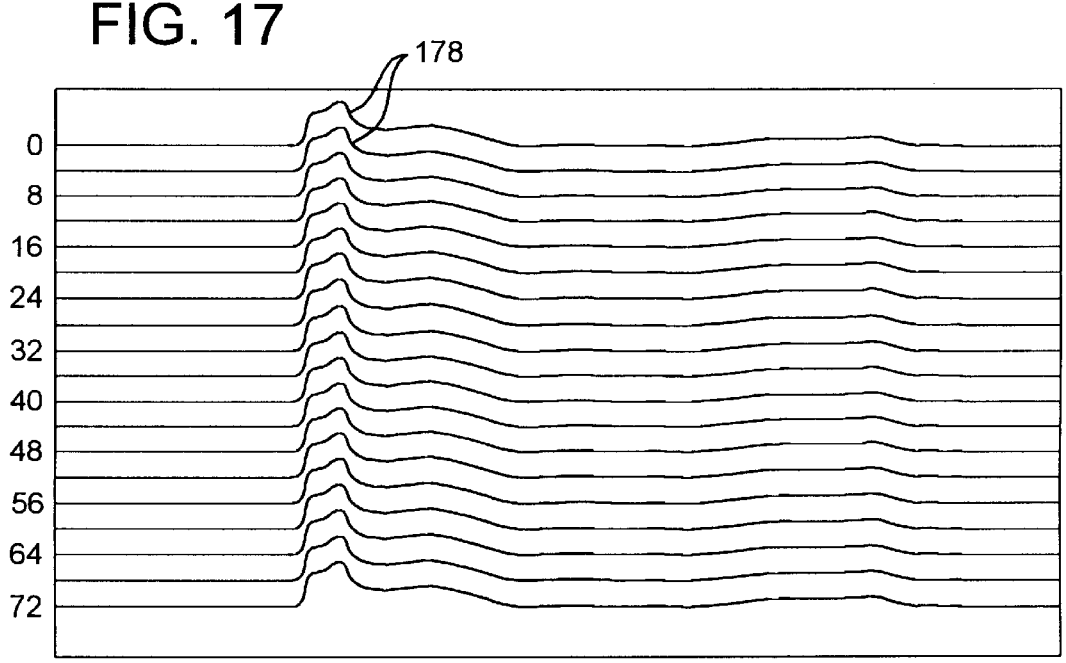
FIG. 17 is a graph illustrating the wave forms in the first step of third embodiment of the present inventions.

Thus, as can be seen in FIG. 17, the first pulse is transmitted at 0 nanoseconds, the next pulse indicating as having a four nanosecond advance, the third pulse at 8 nanoseconds advance, with these advances continuing on down to the 18th pulse which has been advanced by 72 nanoseconds relative to the initial pulse at 0.

Each pulse from the near side antenna 172 passes by the receiving antenna 176, and the pulse is recorded, with the wave forms indicated at 178. It is to be recognized that in most all instances, there is a certain amount of outside electromagnetic, electrical noise, echoes, refractions, etc. that tend to obscure or "clutter" the signal. Each of these pulses 178 is recorded in the memories of the control unit, including all the various extraneous influences on the signal, plus the portion of the signal attributable to the pulse itself. As will be discussed subsequently herein, these pulses 178 that are recorded are used as reference pulses which are subtracted in a subsequent step in the method of the third embodiment.

The next step will now be described with reference to FIG. 18. The far side transmitter is activated so that regularly timed pulses are transmitted from the antenna 174 into the pipe section 170 i.e. without any advancing or delay in the timing. Each transmission at the near side is synchronized with the transmission at the far side. However, each time the near side transmits a pulse, the next pulse from the near side is advanced four nanoseconds from the designated time period from the previous pulse. Thus, at the zero location in FIG. 18, the far side pulse is transmitted at a time period so that the pulses from the near side and far side antennas 174 intersect at the location of the receiving antenna 176. The next pair of pulses are transmitted with the near side pulse being advanced by four seconds, so the point of intersection is spaced two nanoseconds closer to the far side. The third pulse is advanced by eight seconds so that the intersection of the spaced and additional two nanoseconds toward the far side.

It can be seen that the first pair of pulses intersecting at the antenna 176 that the peaks of theses pulses come close to coinciding. It can be seen that subsequent pairs of pulses are transmitted and with the near side pulses being advanced four nanoseconds on each transmission, relative the far side pulse, the pattern of the wave which is received at the antenna 176 comprises a first peak 182 which is attributable to the near side pulse passing by the antenna 176, and a second peak 184 which is attributable to the near side pulse reaching the antenna at a later time.

In this third embodiment, the far side pulse that is received by the antenna 176 is the one which is analyzed to determine whether the corrosion exists. To accomplish this, the following procedure is followed. Each of the wave forms 186 that result from the second step of this method are also stored in memory. Then the wave forms 178 (showed in FIG. 17) are each subtracted from the corresponding wave forms shown in FIG. 18 with the resulting wave forms being shown in at 188, FIG. 20.

Figure 18:
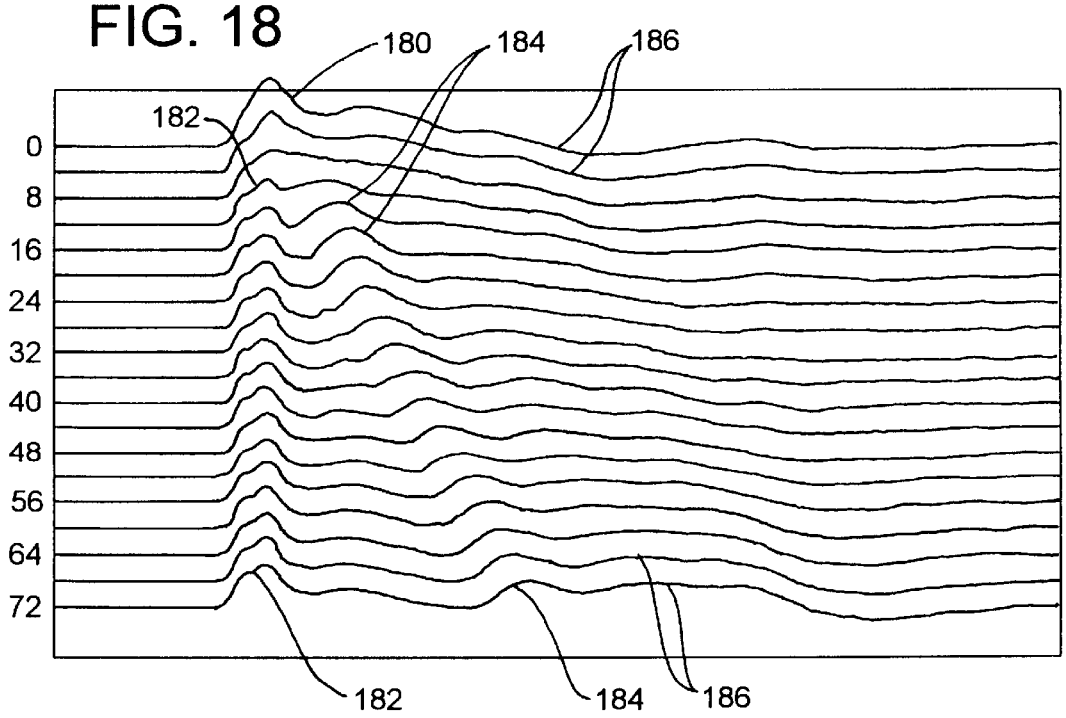
FIG. 18 is a graph similar to FIG. 17, showing the wave forms of a subsequent step in this third embodiment.

What has occurred is that when the wave forms of FIG. 17 are subtracted from the corresponding wave forms of FIG. 18, the wave form from the near side, along with the extraneous noise, echoes, etc. is cancelled out so that what is left is the wave form 188 that essentially represents the far side wave form which is "uncluttered." The overall result is that this facilitates the detection of variations in the wave form that originated from the far side.

It should be noted that if there is a relatively smaller amount of corrosion, its effect on the wave forms which intersect at the location of the corrosion is more difficult to detect. By performing the first three steps as described with reference to FIGS. 17, 18 and 20, these more subtle variations in the wave form resulting from the far side pulse intersecting with the near side pulse at the area of corrosion can be detected more easily.

Figure 20:
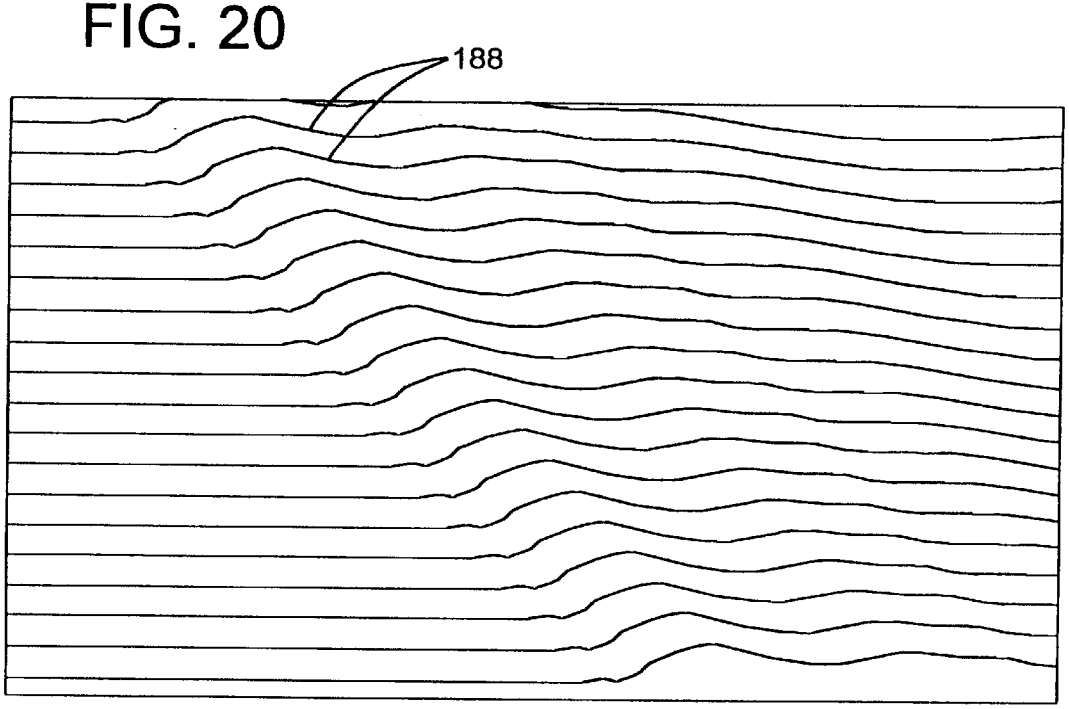
FIG. 20 is a graph similar to FIGS. 17 and 18 illustrating a third step in the third embodiment.
Figure 21:
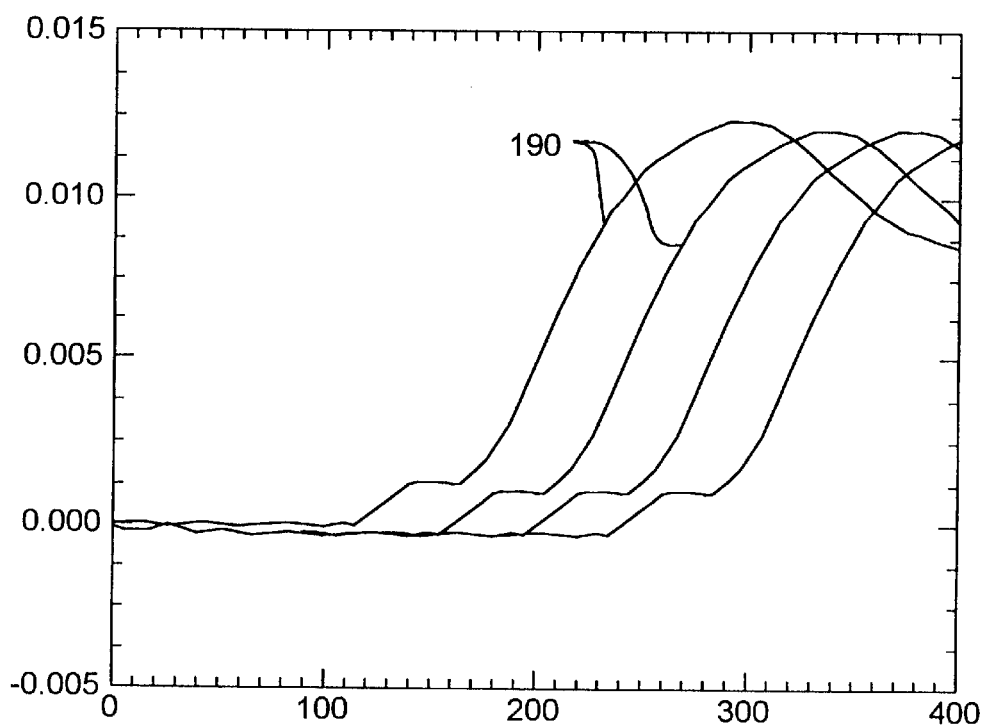
FIG. 21 is a graph showing three of the wave forms of FIG. 20, drawn to a scale emphasizing the vertical dimension of the waves.

FIG. 21 shows four adjacent wave forms 190 which are the same wave forms 188 of FIG. 20, except that vertical dimension has been increased substantially so that the slope of these wave forms 190 is steeper. It can be seen in FIG. 21 that each of these four wave forms 190 are very similar to one another. This would indicate that there is little or no corrosion in the area where the wave forms 190 have intersected.

Figure 22:
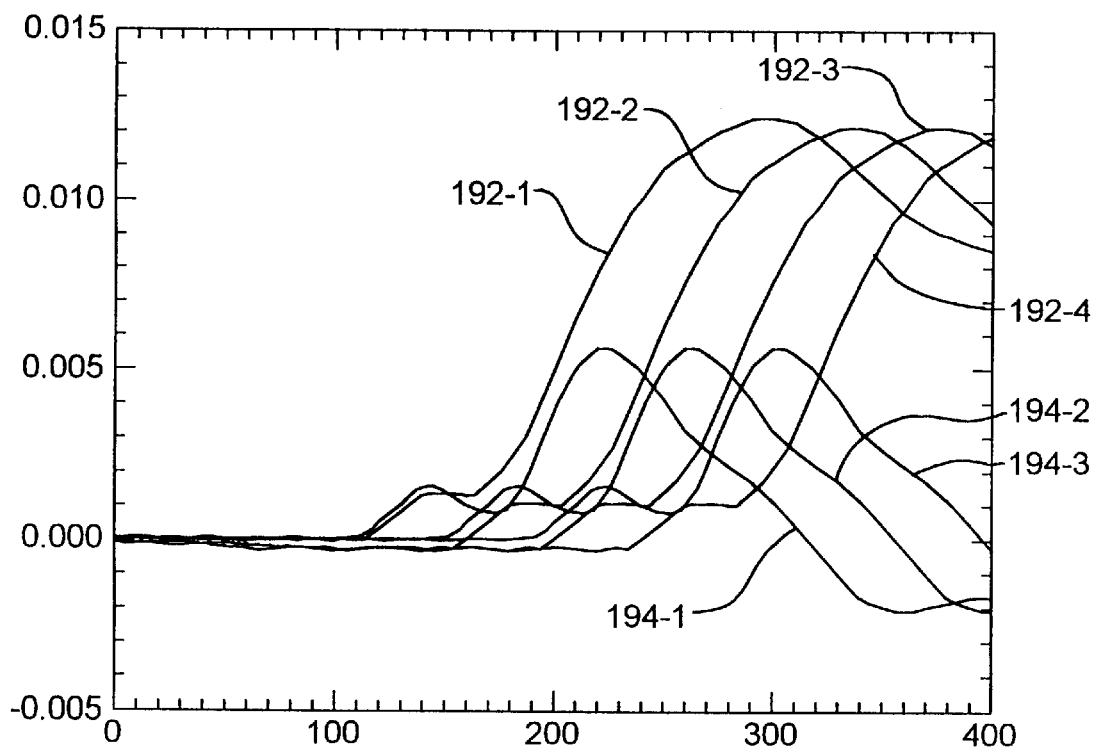
FIG. 22 is a graph similar to FIG. 21 showing the wave forms of FIG. 21 and also the difference wave forms derived therefrom.

Now a fourth step in the method of the present invention is performed to further enhance the ability to analyze the wave forms to detect corrosion, and this will be explained first with reference to FIG. 22. FIG. 22 represents four adjacent wave forms resulting from four pulse transmissions which follow one after the other in sequence. These waves are designated 192-1, 192-2, 192-3 and 192-4. Each wave form is subtracted from the preceding wave to obtain a difference wave form.

This is accomplished by first inverting the wave form 192-2 and then adding this inverted wave form to the wave form 192-1 to obtain a difference wave form which is 194-1 (this 194-1 being the difference wave form of the two wave forms 192-1 and 192-2). In a similar manner, a second difference wave form 194-2 is obtained by inverting the wave form 192-3 and adding this to the wave form 192-2 to obtain the difference wave form 194-2. The third difference wave form 194-3 is obtained in the same way by inverting the wave form 194-4 and adding this to the wave form 192-3.

It can be seen in FIG. 22 that each of the three different wave forms 194-1, 194-2 and 194-3 are very similar to one another and have substantially the same amplitude.

Figure 23:
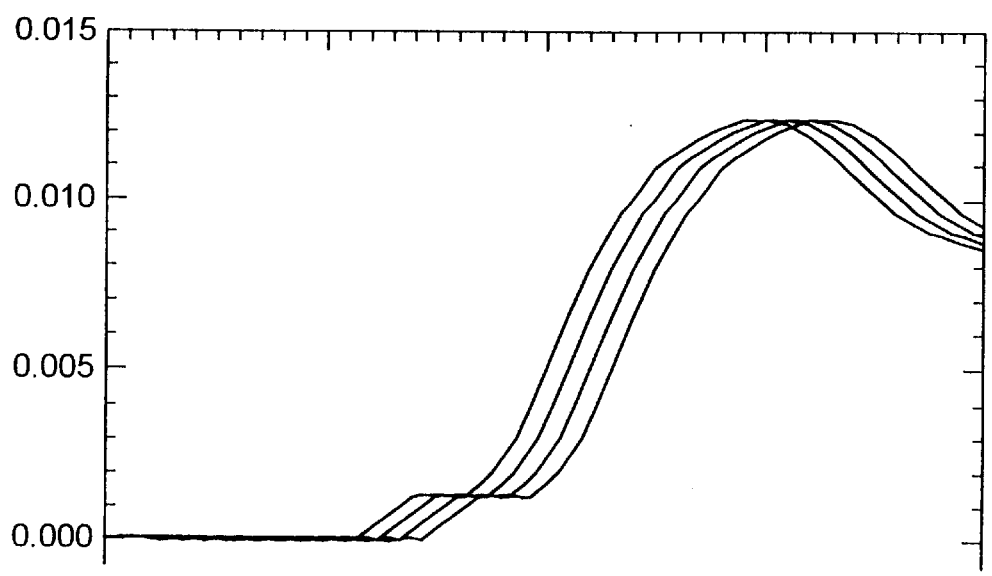
FIG. 23 is a graph similar to FIG. 21 showing three of the waves moved together.

FIG. 23 illustrates another technique utilized in this third embodiment. The four wave forms 194-1 through 194-4 are moved closer together, while leaving the wave forms unchanged. By moving these wave forms closer together, it is much easier to detect variations in the wave forms. Also, the different wave forms which would result from the arrangement of the wave forms in FIG. 23 would be a much smaller anthitude. The effect of this is, however, that differences in amplitude between the peaks does not decrease when the wave forms are moved closer together. This further accentuates the differences in the wave forms.

Figure 24:
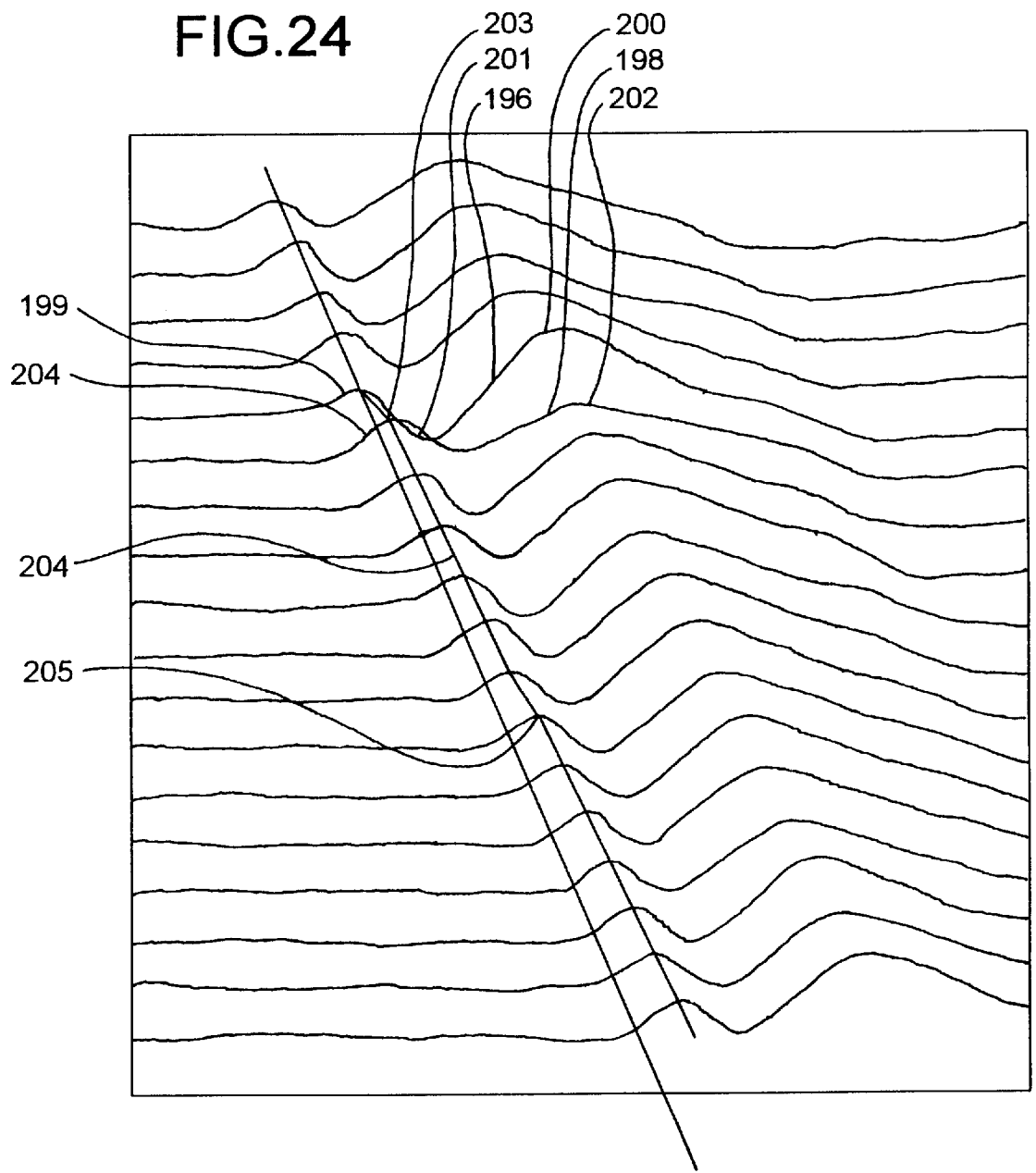
FIG. 24 is a graph showing a plurality of difference wave forms, where two areas of corrosion are being detected.

To illustrate the wave forms where corrosion is being detected, reference is now made to FIG. 24. There are shown 18 adjacent difference wave forms such as shown at 194-1, 194-2, and 194-3 in FIG. 22. It can be seen that the fourth wave form 196 and the fifth wave form 198 are configured rather differently than the adjacent wave forms shown immediately above and below these two wave forms 196 and 198. It will be noted that between the initial "hump" 199 and the second "hump" 200 of the wave form 196 there is a substantial dip at 201.

In addition, it will be noted that the second peak or "hump" 202 of the wave form 198 has a much smaller amplitude. Further, it can be seen that the peak 203 of the first rise or "hump" 204 of the wave form 198 is shifted to the right. An alignment line 205 is drawn to show the shift from the alignment line at the left.

It will also be noted that there is a shift in the peak 206 of a wave form which is the twelfth wave form from the top. This is also an indication of a corrosion, but a smaller degree of corrosion in comparison with the corrosion detected in the area of the fifth and sixth wave forms.

Figure 25:
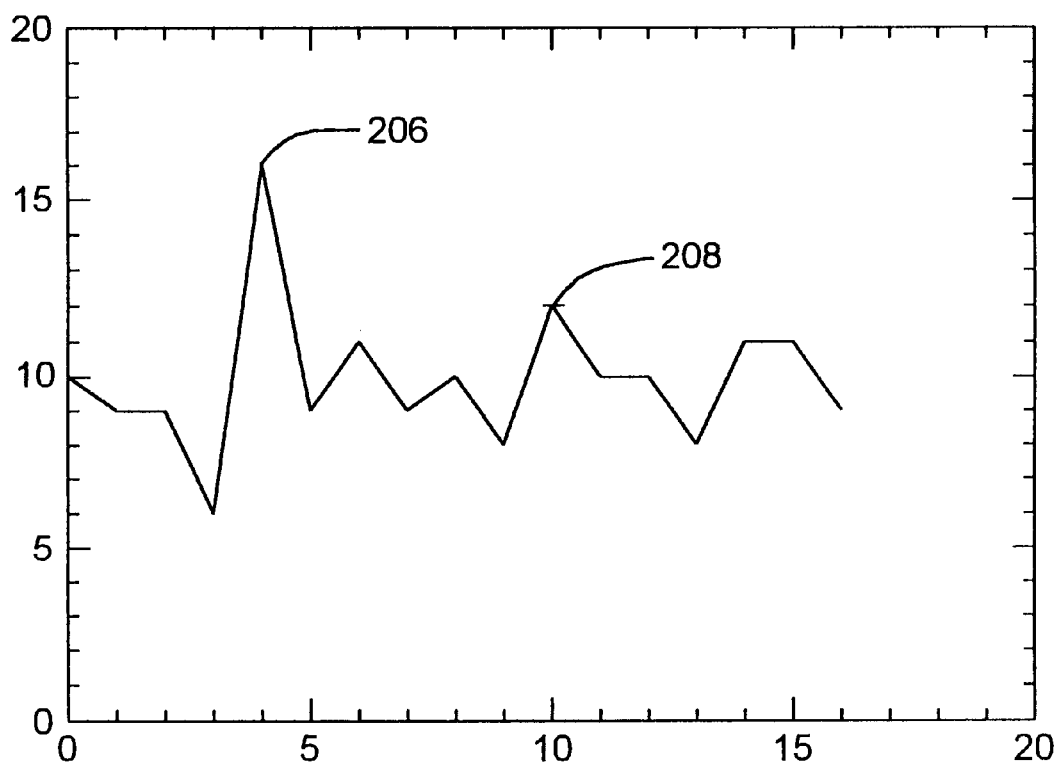
FIG. 25 is a graph derived from the earlier wave forms illustrating the difference in amplitude of the difference waves where corrosion exists.

FIG. 25 is a graph where the points of peak amplitude for adjacent difference wave forms has been prepared by drawing lines connecting adjacent peak points. It can be seen that the peak indicator at 206 is much greater than the rest of the peak points, and this would indicate an area of corrosion. The peak indicated at 208, while not having the height of the peak at 206, still rises above the others. This would indicate that corrosion would likely be encountered at the location at the pipe represented by the point 208 which would be the peak of the difference wave form of two adjacent wave forms where the corrosion was at or near the location of intersection.

Figure 26:
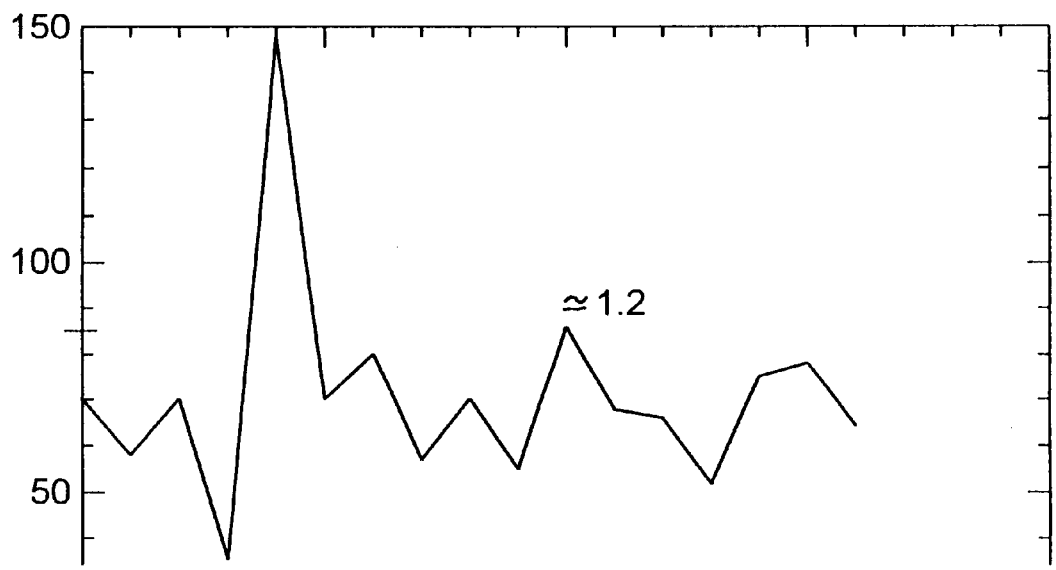
FIG. 26 is a graph based on FIG. 24, further emphasizing the differences in amplitude.

FIG. 26 is a graph similar to FIG. 25, where the amplitude of the points in FIG. 25 have been amplified in a matter to further accentuate the differences.

It is to be understood that the terms "near side" and "far side" can be reversed. Further, it is to be understood that while the third embodiment has been described, with the far side pulse being the pulse which is analyzed, and the near side pulse which has been advanced to cause the point of intersection to be stepped along the elongate number (pipe), this arrangement could be reversed. Further, in an actual testing operation, both the near side pulses arriving at the far side, and the far side pulses arriving at the near side could each be received and analyzed.

Also, it is to be understood that various modifications to be made in the present invention without departing from the basic teachings thereof. Further, the terminology used in this description should, in the following claims, be given an interpretation commensurate with the scope of the invention and should not be interpreted as being limited to the specific procedures and operating components described herein.

Now therefore I claim:

1. A method of identifying corrosion on an electromagnetically permeable elongate member, said method comprising:

a. transmitting near side and far side electric or electromagnetic pulses (waves) from, respectively, near side and far side spaced transmitting locations on said elongate member, with said pulses (waves) travelling toward one another to intersect at intersecting locations on said elongate member;

b. receiving said far side pulses (waves) as wave forms at a receiving location after intersection with related near-side pulses (waves);

c. synchronizing transmission of the near side and far side pulses (waves) so that the intersections of the near side and far side pulses (waves) occur at spaced intersecting locations on said elongate member;

d. combining the wave forms of at least two of said far side pulse wave which are spaced from one another to form a composite wave form;

e. ascertaining a variation or variations in said composite wave form as a means of detecting corrosion.

2. The method as recited in claim 1, wherein one of the wave form of the two wave forms that are to be combined is inverted and then added to the other of the wave forms being combined to create a difference wave form, and variations in said difference wave form are ascertained as a means of detecting corrosion.

3. The method as recited in claim 2, wherein far side pulses which pass through points of intersection that are adjacent to one another are considered to be sequential far side pulses, with the order of sequence being the same as the order in which the points of intersection are spaced along the elongate member, and combining of the far side wave forms is accomplished in a pattern such that first and second adjacent wave forms are combined to make a first composite wave form, the second wave form and an adjacent third wave form are combined to make a second composite wave form, the third wave form is combined with an adjacent fourth wave form to make a third composite wave form, with the pattern repeating itself with subsequent pairs of wave forms from adjacent far side pulses.

4. The method recited in claim 3, wherein adjacent composite wave forms are compared with one another as a means of detecting corrosion.

5. The method as recited in claim 4, wherein a reference wave form is established by creating composite wave forms resulting from pulses that intersect away from a corroded areas of the elongate member and identifying composite wave forms that differ from the reference composite wave form in phase shift and/or dispersion and/or amplitude and/or wave distortion.

6. The method as recited in claim 5, wherein corrosion that is present between two adjacent points of intersection on the elongate member, is detected by examining a composite wave form resulting from combining the difference wave form overlapping the point of intersection with difference wave forms on opposite sides of the overlapping composite wave form.

7. The method as recited in claim 5, wherein corrosion is present at a point of intersection of two wave forms, and two difference wave forms are derived by combining the wave form at the point of corrosion with adjacent wave forms, and these are compared with one another wave form to ascertain corrosion.

8. The method as recited in claim 7 wherein two additional difference wave forms that are on opposite sides of, and adjacent to, the two wave forms which are compared to detect the corrosion are also compared with the two difference wave forms which are combined at the point of intersection, as a means of detecting corrosion.

9. The method as recited in claim 1, wherein a far side pulses which pass through the points of intersection that are adjacent to one another are considered to be sequential far side pulses, with the order of sequence being the same as the order in which the points of intersection are spaced along the elongate member, the combining of the far side wave forms being accomplished in a pattern such that the wave form resulting from the first and second adjacent nearside pulses intersecting with related far side pulses are combined to make a first composite wave form, wave forms of the second and third near side pulses that are combined with the related far side pulses are combined to make composite wave forms, with this pattern repeating itself for subsequent pulses.

10. The method as recited in claim 1, wherein said pulses (waves) comprise earlier and later arrival wave components, said method further comprising ascertaining said variation or variations at least in part in said later arrival wave components.

11. The method as recited in claim 10, wherein said later wave components comprise wave component arrivals at least as much as 200 nanoseconds later than initial arrival of said earlier arrival wave components.

12. The method as recited in claim 10, wherein said later wave components comprise wave component arrivals at least as much as 400 seconds later than initial arrival of said earlier arrival wave components.

13. The method as recited in claim 1, wherein said far side wave forms comprise an initial higher amplitude portion and later higher amplitude portions, said method comprising analyzing at least in part one or more variation or variations of one or more of said later high amplitude wave portions.

14. The method as recited in claim 13, wherein said variation or variations of one or more of the later higher amplitude portions are ascertained as a phase shift or shifts, amplitude variation or variations, or both phase shift and amplitude variation or variations.

15. The method as recited in claim 13, wherein amplitude variations are ascertained.

16. The method as recited in claim 13, wherein phase shift variation or variations are ascertained.

17. The method as recited in claim 1, wherein the wave forms of far side pulses (waves) that are received at the receiving location comprise also wave form components of said near side pulses (waves), said method further comprising subtracting said wave form components of the near side pulses (waves) from said wave forms of the far side pulses (waves) to substantially remove the near side form components from the composite wave form.

18. The method as recited in claim 17, wherein the wave forms received at the receiving locations which comprise wave forms of the far side pulses (waves) and also wave components of the near side pulses (waves) are subtracted from one another in timed relationship so that the near side wave form components are subtracted from one another to substantially remove the nearside wave form components, and the wave forms of the far side pulses (waves) that are combined are subtracted from one another with the wave forms of the far side pulses (waves) being spaced from one another in time to form said composite waves.

19. The method as recited in claim 17, wherein at least one of said near side pulses (waves) is provided at said receiving location as a near side reference wave and the near side reference wave is subtracted from the wave forms of the far side pulses (waves) that are received at the receiving location and which also comprise wave form components of said near side pulses (waves), to substantially remove the near side wave components from the far side wave forms.

20. A method of identifying corrosion on an electronmagnetically permeable elongate member, said method comprising:

a) transmitting near side and far side electric or electromagnetic pulses (waves) from, respectively, near side and far side spaced transmitting locations on said elongate member, with said pulses (waves) traveling toward one another to intersect at intersecting locations on said elongate member;

b) receiving said far side pulses as wave forms at a receiving location after intersection with related nearside pulses (waves);

c) synchronizing transmission of the near side and far side pulses (waves) so that the intersections of the near side and far side pulses (waves) occur at spaced intersecting locations on said elongate member;

d) providing one or more inverted near side reference wave forms and combining said one or more inverted near side reference wave forms to the far side wave forms received at the receiving location to remove near side wave components from the far side wave forms to provide modified far side wave forms; and e) ascertaining a variation or variations in said modified far side wave forms as a means of detecting corrosion.

21. The method as recited in claim 20, wherein two of said modified far side wave forms which are spaced in time from one another are combined to form a composite wave form, and analyzing said composite wave form to find a variation or variations in the far side wave forms.

22. The method as recited in claim 21, wherein one of the modified forms of the tow modified wave forms that are to be combined is inverted and then added to the other of the modified wave forms being combined to create a difference wave form, and variations in said difference wave form are ascertained as a means of detecting corrosion.

23. The method as recited in claim 22, wherein far side pulses which pass through points of intersection that are adjacent to one another are considered to be sequential far side pulses, with the order of sequence being the same as the order in which the points of intersection are spaced along the elongate member, and combining of the far side wave forms is accomplished in a pattern such that first and second adjacent wave forms are combined to make a first composite wave form, the second wave form and an adjacent third wave form are combined to make a second composite wave form, the third wave form is combined with an adjacent fourth wave form to make a third composite wave form, with the pattern repeating itself with subsequent pairs of wave forms from adjacent far side pulses.

24. The method recited in claim 23, wherein adjacent composite wave forms are compared with one another as a means of detecting corrosion.

25. The method as recited in claim 24, wherein a reference wave form is established by creating composite wave forms resulting from pulses that intersect away from a corroded areas of the elongate member and identifying composite wave forms that differ from the reference composite wave form in phase shift and/or dispersion and/or amplitude and/or wave distortion.

26. The method as recited in claim 25, wherein corrosion that is present between two adjacent points of intersection on the elongate member, is detected by examining a composite wave form resulting from combining the difference wave form overlapping the point of intersection with difference wave forms on opposite sides of the overlapping composite wave form.

27. The method as recited in claim 25, wherein corrosion is present at a point of intersection of two wave forms, and two difference wave forms are derived by combining the wave form at the point of corrosion with adjacent wave forms, and these are compared with one another wave form to ascertain corrosion.

28. The method as recited in claim 27 wherein two additional difference wave forms that are on opposite sides of, and adjacent to, the two wave forms which are compared to detect the corrosion are also compared with the two difference wave forms which are combined at the point of intersection, as a means of detecting corrosion.

29. The method as recited in claim 22, wherein a far side pulses which pass through the points of intersection that are adjacent to one another are considered to be sequential far side pulses, with the order of sequence being the same as the order in which the points of intersection are spaced along the elongate member, the combining of the far side wave forms being accomplished in a pattern such that the wave form resulting from the first and second adjacent nearside pulses intersecting with related far side pulses are combined to make a first composite wave form, wave forms of the second and third near side pulses that are combined with the related far side pulses are combined to make composite wave forms, with.

30. The method as recited in claim 21, wherein said pulses (waves) comprise earlier and later arrival wave components, said method further comprising ascertaining said variation or variations at least in part in said later arrival wave components.

31. The method as recited in claim 30, wherein said later wave components comprise wave component arrivals at least as much as 200 nanoseconds later than initial arrival of said earlier arrival wave components.

32. The method as recited in claim 30, wherein said later wave components comprise wave component arrivals at least as much as 400 seconds later than initial arrival of said earlier arrival wave components.

33. The method as recited in claim 20, wherein said far side wave forms comprise an initial higher amplitude portion and later higher amplitude portions, said method comprising analyzing at least in part one or more variation or variations of one or more of said later high amplitude wave portions.

34. The method as recited in claim 33, wherein said variation or variations of one or more of the later high amplitude portions are ascertained as a phase shift or shifts, amplitude variation or variations, or both phase shift and amplitude variation or variations.

35. The method as recited in claim 33, wherein amplitude variations are ascertained.

36. The method as recited in claim 33, wherein phase shift variation or variations are ascertained.

37. The method as recited in claim 20, wherein the wave forms received at the receiving locations which comprise wave forms of the far side pulses (waves) and also wave components of the near side pulses (waves) are subtracted from one another in timed relationship so that the near side wave form components are subtracted from one another to substantially remove the nearside wave form components, and the wave forms of the far side pulses (waves) that are combined are subtracted from one another with the wave forms of the far side pulses (waves) being spaced from one another in time to form said composite waves.

38. The method as recited in claim 20, wherein at least one of said near side pulses (waves) is provided at said receiving location as a near side reference wave and the near side reference wave is subtracted from the wave forms of the far side pulses (waves) that are received at the receiving location and which also comprise wave form components of said near side pulses (waves), to substantially remove the near side wave components from the far side wave forms.

* * * * *